US010974074B2

(12) United States Patent
Hale et al.

(10) Patent No.: US 10,974,074 B2
(45) Date of Patent: Apr. 13, 2021

(54) MULTI-PURPOSE OBJECT FOR A PATIENT PLANNING AND TREATMENT SYSTEM

(71) Applicant: Vision RT Limited, London (GB)

(72) Inventors: Gideon M. Hale, London (GB); Benjamin James Waghorn, London (GB)

(73) Assignee: VISION RT LIMITED, London (GB)

( * ) Notice: Subject to any disclaimer, the term of this patent is extended or adjusted under 35 U.S.C. 154(b) by 0 days.

(21) Appl. No.: 16/277,458

(22) Filed: Feb. 15, 2019

(65) Prior Publication Data

US 2019/0255358 A1 Aug. 22, 2019

(30) Foreign Application Priority Data

Feb. 16, 2018 (GB) .................................. 1802597.3

(51) Int. Cl.
| | | |
|---|---|---|
| *A61N 5/10* | (2006.01) | |
| *A61B 6/00* | (2006.01) | |
| *G06T 7/73* | (2017.01) | |
| *G06T 7/593* | (2017.01) | |
| *A61B 90/00* | (2016.01) | |

(52) U.S. Cl.
CPC ............ *A61N 5/1049* (2013.01); *A61B 6/583* (2013.01); *A61N 5/103* (2013.01); *A61N 5/1045* (2013.01); *A61N 5/1075* (2013.01); *A61B 2090/3937* (2016.02); *A61B 2090/3966* (2016.02); *A61N 5/1064* (2013.01); *A61N 5/1081* (2013.01); *A61N 2005/105* (2013.01); *A61N 2005/1059* (2013.01); *A61N 2005/1076* (2013.01); *G06T 7/593* (2017.01); *G06T 7/75* (2017.01); *G06T 2200/08* (2013.01)

(58) Field of Classification Search
CPC .... A61N 5/1049; A61N 5/103; A61N 5/1045; A61N 5/1075; A61N 5/1064; A61N 5/1081; A61B 2090/3937; A61B 2090/3966; G06T 7/75; G06T 7/593
USPC .......................................................... 378/65
See application file for complete search history.

(56) References Cited

U.S. PATENT DOCUMENTS

| | | | |
|---|---|---|---|
| 7,056,019 B1 * | 6/2006 | Hanson ................. | A61B 6/583 |
| | | | 378/18 |
| 7,348,974 B2 | 3/2008 | Smith et al. | |
| 7,889,906 B2 | 2/2011 | Smith et al. | |
| 8,135,201 B2 | 3/2012 | Smith et al. | |

(Continued)

OTHER PUBLICATIONS

Grimm et al., "A quality assurance method with submillimeter accuracy for stereotactic linear accelerators," Journal of Applied Clinical Medical Physics, vol. 12, No. 1, 2011, pp. 182-198.

(Continued)

*Primary Examiner* — Taeho Jo
(74) *Attorney, Agent, or Firm* — Birch, Stewart, Kolasch & Birch, LLP.

(57) ABSTRACT

A multi-purpose object for calibrating, monitoring and/or tracking a patient in a treatment system and/or a treatment planning system is described, the multi-purpose object being made of transparent material and defining an internal space having one or more targets, wherein an upper surface is coated so as to define a pattern of transparent markings. The interior of the multi-purpose object can be back lit to present a high contrast surface image for a patient treatment, tracking or monitoring system.

17 Claims, 13 Drawing Sheets

(56) References Cited

U.S. PATENT DOCUMENTS

| | | | |
|---|---|---|---|
| 9,028,422 B2 | 5/2015 | Meir et al. | |
| 9,606,054 B2* | 3/2017 | King | G01N 21/3586 |
| 9,736,465 B2 | 8/2017 | Hanson et al. | |
| 10,119,922 B2* | 11/2018 | Bernard | G01N 23/04 |
| 2001/0036245 A1* | 11/2001 | Kienzle, III | A61B 17/1721 |
| | | | 378/4 |
| 2003/0207441 A1* | 11/2003 | Eyster | G01N 33/54386 |
| | | | 435/287.1 |
| 2004/0136706 A1* | 7/2004 | Takahashi | G03B 13/04 |
| | | | 396/281 |
| 2005/0078801 A1* | 4/2005 | Georgeson | G01T 1/169 |
| | | | 378/207 |
| 2007/0018077 A1* | 1/2007 | Puscasu | G01J 1/42 |
| | | | 250/210 |
| 2008/0012850 A1* | 1/2008 | Keating, III | H04N 13/393 |
| | | | 345/419 |
| 2008/0093544 A1 | 4/2008 | Wang et al. | |
| 2008/0212737 A1* | 9/2008 | D'Souza | A61N 5/1049 |
| | | | 378/65 |
| 2009/0139297 A1* | 6/2009 | Lu | G12B 13/00 |
| | | | 73/1.01 |
| 2009/0161833 A1* | 6/2009 | Skuse | G01N 23/04 |
| | | | 378/207 |
| 2009/0190723 A1* | 7/2009 | Jang | A61B 6/5276 |
| | | | 378/207 |
| 2009/0238338 A1* | 9/2009 | Long | A61N 5/1049 |
| | | | 378/65 |
| 2010/0141776 A1* | 6/2010 | Ban | G06T 7/80 |
| | | | 348/187 |
| 2013/0258353 A1* | 10/2013 | Kosmecki | G01B 21/042 |
| | | | 356/616 |
| 2014/0049629 A1* | 2/2014 | Siewerdsen | A61B 34/20 |
| | | | 348/77 |
| 2015/0265852 A1 | 9/2015 | Meir et al. | |
| 2016/0129283 A1 | 5/2016 | Meir et al. | |
| 2016/0332000 A1* | 11/2016 | Hale | A61N 5/1075 |
| 2017/0080254 A1* | 3/2017 | Scheib | A61N 5/1071 |
| 2018/0014809 A1* | 1/2018 | Lin | A61B 6/584 |
| 2018/0020206 A1* | 1/2018 | Sheridan | H04N 13/239 |
| 2018/0231465 A1* | 8/2018 | Rothberg | C12Q 1/6874 |
| 2018/0339173 A1* | 11/2018 | Kilby | A61N 5/1083 |
| 2019/0387958 A1* | 12/2019 | Kimpe | A61B 5/444 |

OTHER PUBLICATIONS

Low et al., "Minimization of target positioning error in accelerator-based radiosurgery," Medical Physics, vol. 22, No. 4, Apr. 1995, pp. 443-448.

Lutz et al., "A System for Stereotactic Radiosurgery with a Linear Accelerator," Int. J. Radiation Oncology Biol. Phys., vol. 14, No. 2, Feb. 1988, pp. 373-381.

Schreibmann et al., "Automated Quality Assurance for Image-Guided Radiation Therapy," Journal of Applied Clinical Medical Physics, vol. 10, No. 1, 2009, pp. 71-79.

* cited by examiner

MULTI-PURPOSE OBJECT FOR A PATIENT PLANNING AND TREATMENT SYSTEM

The present invention concerns a calibration object for calibrating a patient monitoring system for monitoring the location of a patient with very high accuracy such as a patient monitoring system for monitoring the positioning and location of a patient during radiotherapy. In more detail, the disclosure concerns a multi-purpose object which can be used in patient planning systems and patient treatment systems for monitoring and/or tracking patients.

Radiotherapy consists of projecting onto a predetermined region of a patient's body, a radiation beam so as to destroy or eliminate tumors existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful. For this reason, a number of monitoring systems for assisting the positioning of patients during radiotherapy have been proposed such as those described in Vision RT's earlier patents and patent applications in U.S. Pat. Nos. 7,889,906, 7,348,974, 8,135,201, 9,028,422, 9,736,465 and US Pat Application Nos. 2015/265852 and 2016/129283.

In the systems described in Vision RT's patents and patent applications, images of a patient are obtained and processed to generate data identifying 3D positions of a large number of points corresponding to points on the surface of a patient. Such data can be compared with data generated on a previous occasion and used to position a patient in a consistent manner or provide a warning when a patient moves out of position. Typically, such a comparison involves undertaking Procrustes analysis to determine a transformation which minimizes the differences in position between points on the surface of a patient identified by data generated based on live images and points on the surface of a patient identified by data generated on a previous occasion.

Vision RT's patient monitoring systems are able to generate highly accurate (e.g. sub millimeter) models of the surface of a patient. To do so, the monitoring system is calibrated in order to establish the relative locations and orientations of the image capture devices/cameras as well as intrinsic internal camera parameters such as any optical distortion caused by the optical design of the lens of each image detector/camera e.g. barrel, pincushion, and moustache distortion and de-centering/tangential distortion, and other internal parameters of the cameras/image capture devices (e.g. focal length, image center, aspect ratio skew, pixel spacing etc.). Once known, the internal camera parameters can be utilized to manipulate obtained images to obtain images free of distortion. 3D position measurements can then be determined by processing images obtained from different locations and deriving 3D positions from the images and the relative locations and orientations of the image capture devices/cameras.

Calibration of a monitoring system is normally a multi-step process.

In one approach, the location of the treatment room iso-center is identified as described in Lutz W, Winston K R, Maleki N. A system for stereotactic radiosurgery with a linear accelerator. Int J Radiat Oncol Biol Phys. 1988; 14(2):373-81 in which a calibration phantom comprising a small metallic ball made of steel, titanium or tungsten is fixed on a treatment table by a locking mechanism with the phantom position being adjustable in three directions by means of a micrometer tool. The collimator used for radiotherapy is attached to the gantry head and the ball is placed as closely as possible to an estimated location of the treatment room iso-center. A collimated beam is then used to expose a radiographic test film mounted perpendicular to the beam direction on a stand behind the ball. Differences between the center of the sphere shadow and the field center identifies the differences between the estimated iso-center and the true iso-center and an offset is read on each film using transparent template guidance scales or by scanning the film and software analysis such as is discussed in Low D A, Li Z, Drzymala R E. Minimization of target positioning error in accelerator-based radiosurgery. Med Phys. 1995; 22(4):443-48 and Grimm S L, Das I J, et al. A quality assurance method with sub-millimeter accuracy for stereotactic linear accelerators. J Appl Clin Med Phys. 2011; 12(1):182-98 and E Schriebmann, E Elder and T Fox, Automated Quality Assurance for Image-Guided Radiation Therapy, J Appl Clin Med Phys. 2009:10(1):71-79.

The position of the calibration phantom can then be adjusted based on the analysis of the radiographic Winston Lutz images, until the phantom is accurately located at the treatment room iso-center. Having identified the location of the iso-center, the location of the iso-center can then be highlighted by using a set of lasers generating planes of laser lights and to that end many calibration phantoms have exterior markings so that once the phantom has been located at the iso-center, laser lights can be adjusted so that generated planes of laser light coincide with the exterior markings and when the phantom is removed, the location of the iso-center is identified by the intersection of the laser beams.

Having identified the location for the treatment room iso-center, a set of internal parameters for cameras monitoring the area in the vicinity of the iso-center are then determined enabling images captured by the cameras to be processed to identify measurements in 3D space.

Typically, a calibration object bearing a known pattern of markings, such as a rigid plate of aluminum or steel with markings defining a matrix of circles at known positions on the surface of the plate is placed relative to iso-center on the mechanical couch and imaged by the cameras of the monitoring system. The positioning of the markings at known positions needs to be highly accurate. To achieve this, typically such markings are screen printed onto the plate. This and the rigidity of the calibration plate ensures that the relative positioning of the markings corresponds to the underlying assumptions of the positioning of the markings and hence enables distortions in images to be identified and the monitoring system to associate distances in images with physical measurements in the real world.

The images of the plate obtained by the cameras are then processed to identify the locations of the circles appearing in the images and to determine a projective transformation to account for the surface being viewed at an oblique angle. A suitable transformation can then be applied to correct the image so as to generate a representation of the calibration object without that distortion. The relative locations of the circles as they appear in the corrected image and the extent to which they deviate from a regular grid can then be used to identify any lens irregularities present in the camera system and to relate distances in the images to real world distances.

The positioning of the cameras relative to the iso-center of the treatment apparatus can then be determined by imaging a different calibration object, typically a calibration cube positioned on a treatment apparatus at a position with its center at the iso-center of the treatment apparatus. This is typically achieved by the calibration cube bearing a series of markings on its exterior which enable the calibration cube to be positioned with its center co-incident with the treatment room iso-center by aligning the markings with the laser lights used to highlight the iso-center. Images of the cube are then obtained and processed to generate a model representation of the surface of the cube in model space. The center of the model representation then identifies the location of the treatment room iso-center in model space and the relationship between the co-ordinates in model space and real-world distances can be determined by comparing the generated model surface with the known dimensions of the calibration cube. This in turn enables the relative locations of cameras in the monitoring system in 3D space to be determined.

Vision RT proposed a modified approach to calibrating a monitoring system in US Patent Application US 2016/129283 which avoided reliance upon a treatment room iso-center being identified by intersection of planes of laser light. In such an approach, initially the relative positioning and intrinsic camera parameters of a camera system are determined using a calibration sheet as described above enabling the camera system to remove image distortions from images captured by the cameras and utilize the processed images to create a 3D model of imaged surfaces.

A calibration phantom in the form of a calibration cube containing irradiation targets, such as one or more small ceramic or metallic balls or other ceramic or metal targets such as targets made of steel, titanium or tungsten or the like, then is positioned with the phantom's center at an estimated location for the iso-center of a radiotherapy treatment apparatus with the choice of material being dependent upon the nature of the radiation being applied by the treatment apparatus (e.g. ceramic targets may be imaged utilizing MV or kV radiation whereas metal targets show up better when radiated with MV radiation but worse when irradiated with kV radiation). The calibration phantom is then irradiated using the radiotherapy treatment apparatus. The relative location of the center of the calibration phantom and the iso-center of the radiotherapy treatment is then determined by analyzing radiographic images of the irradiation of the calibration phantom containing the irradiation targets. In other word, the known calibration methods is a two-step procedure, where two different calibration objects (a cube with irradiation targets, and a calibration sheet) may be needed. Thus, a calibration object with irradiation targets is needed to estimate the transformation that aligns a computer model coordinate system with an iso-center of the treatment room, and a calibration sheet is needed to calibrate the camera system intrinsic and extrinsic to the treatment room.

In some systems, the calibration phantom is then repositioned by, for example, sending instructions to a moveable couch on which the calibration phantom is mounted so as to apply an offset corresponding to the determined relative location of the center of the calibration phantom from the iso-center of the radio therapy treatment apparatus. The relative location of the cameras of the monitoring system and the treatment room iso-center can then be determined by capturing images of the repositioned calibration cube positioned so as to have its center located at the treatment room iso-center.

Alternatively, the relative locations of the cameras and the treatment room iso-center could be determined without physically relocating the calibration cube. More specifically, the calibration cube could be positioned in the manner described above at an estimated location for the iso-center of a radio therapy treatment apparatus. Images of the calibration cube are then obtained and a 3D computer model of the surface of the cube could then be generated. The calibration cube could also be irradiated without the cube being repositioned and radiographic images of the irradiated cube and in particular irradiation targets within the cube could be obtained and processed to determine the relative location of the cube and the treatment room iso-center. The location of the treatment room iso-center relative to the positions of the cameras of the monitoring system could then be determined based on any offset determined by analyzing the radiographic images and the representation of the cube in model space generated by processing images captured by the monitoring apparatus.

Either approach improves the accuracy with which a monitoring system can subsequently monitor the positioning and movement of a patient as either approach avoids errors arising from a laser lighting system potentially misidentifying the location of the treatment room iso-center.

Due to the requirement for very high accuracy and the sensitivity of the monitoring systems for monitoring patient positioning, it is necessary to calibrate and re-calibrate a monitoring system repeatedly in order to ensure that the system parameters have been measured accurately and to identify any changes within the system.

Although existing approaches to calibrating patient monitoring system for use with a radio therapy treatment apparatus as described above are highly accurate, they require the use of a calibration cube and a calibration plate, that is two separate components, which not only increases the overall component cost, but also storage and shipping costs. Furthermore, the calibration features or markings are applied to the calibration plate by screen printing which is an expensive process.

Improvements in calibration components and methods are therefore desirable. Furthermore, improvements in objects used for calibration of treatment monitoring systems, and which could also be used in e.g. treatment planning systems, such as CT and/or MR imaging modalities is needed. Therefore, in the following a multi-purpose object, which can be used in different modalities, and especially as a multi-purpose calibration object is described. It should be noted that throughout the disclosure a patient treatment planning system is used to define at least one of a scanning modality, such as CT or MR, whereas a treatment system covers e.g. radiotherapy and proton therapy treatment delivery systems, wherein the multi-purpose object can be used in different ways in the different systems.

In accordance with one aspect of the present invention there is provided a calibration object for calibrating a patient monitoring system, the calibration object comprising a transparent material inner portion and an outer portion substantially covering the transparent material inner portion, the transparent material inner portion having a plurality of sides defining an internal space, wherein at least part of the outer portion covering at least one of the plurality of sides of the transparent material inner portion is removed to reveal the transparent material inner portion the portions of the outer portion which are removed thereby defining a pattern of calibration markings on the exterior of the calibration object. (Old claim 1)

The calibration object could also be contemplated as a multi-purpose object for a patient treatment system and/or a treatment planning system. That means, at least parts of the object, could be utilized in e.g. a CT scanning setup, wherein a couch movement tracking is of interest. In such setup at least a part of the multi-purpose object, e.g. a part of the calibration object, could be applied to track the movement of a couch in any treatment room. Such multi-purpose object comprises in more detail a first section, wherein the first section comprises a surface configured with a plurality of transparent markings. These transparent markings could be contemplated as the same as the pattern of calibration markings on the exterior of the calibration object described in this disclosure. Thus, the calibration markings, may be used for both calibration purposes and tracking purposes in an imaging system of a patient treatment system.

The multi-purpose object furthermore in an embodiment comprises a second section having one or more recess(es) configured with a depth and a width, wherein each of the one or more recess(es) is configured to contain a target object, and wherein the first section is configured to be arranged on top of the said second section. This configuration allows for a multi-purpose object which can be used for calibration of a camera system to an iso-center of a treatment room, while at the same time being used for monitoring and tracking of a patient or other component, such as a couch in a treatment room.

In an embodiment, where the multi-purpose object comprises one or more targets, the one or more target objects is configured as radio-opaque targets, to ensure that the targets can be irradiated in a treatment room so that the targets appears on an irradiated image obtained of the irradiated targets.

Furthermore, the applicants have appreciated that the manner in which a monitoring system is calibrated has an impact on the accuracy of the system. Monitoring systems such as those used to monitor patients undergoing radiotherapy are very sensitive to changes in the positioning and orientation of image detectors used to monitor patients. Typically, a patient monitoring system is located a distance (e.g. 1 to 2 meters) away from a patient being monitored so as allow space for a treatment apparatus to move and apply radiation to a patient from a variety of different angles and positions. This separation between the monitoring system and a patient being monitored means that very small variations in the position and orientation of the image detectors are magnified which can impede the accuracy of a monitoring system which otherwise is able to monitor the positioning of a patient to sub-millimeter accuracy.

By providing a calibration object with a transparent inner portion and an opaque outer portion, parts of which are machined away to reveal the transparent inner portion and illuminating the interior of the calibration object either by using an external light source or providing a light source within the calibration object, this creates a high contrast between transparent calibration markings and the outer portion, and therefore enable high quality images of the calibration markings to be obtained. In other words, by providing a multi-purpose object with a first section wherein the first section comprises a surface configured with a plurality of transparent markings, it is possible to create a pattern enabling a high contrast between the transparent markings and an opaque outer portion, covering areas different from the areas of the transparent markings on the multi-purpose object.

In one embodiment, the outer portion comprises a coating and the calibration markings and/or the positioning markings are created by removing the coating by etching using a precision machining process to expose the transparent material inner portion. In more detail, the multi-purpose object may be configured with the second section and the first section, which is made from a transparent material, wherein at least one or more of a surface of the second and/or the first section is configured with a coating, wherein at least one coating material is covering the one or more surfaces at areas different from positions of the transparent markings. The multi-purpose object whit such configuration may be created by applying the outer coating to at least the first section, and subsequently removing the coating from areas known to contain the transparent markings. This process could e.g. be done by precision etching to reveal the transparent inner portion of the first and second sections, to which the coating may be applied.

In a further embodiment, the coating applied to a surface of at least the first section (and/or potentially also to a surface of the second section) is a coating material configured to cover areas at positions of the transparent markings, wherein the coating material, which cover the transparent markings, comprises a first light-reflective coating configured to reflect light incident on an internal space of said first and/or second section. Thus, the transparent markings are configured to emit light exposed to the markings when the multi-purpose object is positioned in the treatment room.

In other word, the multi-purpose object (i.e. the calibration object) comprises a first light-reflective coating applied to the transparent material inner portion to substantially reflect light incident in the internal space from a light source so as to illuminate the calibration object, and the known pattern of calibration markings is removed from the first light-reflective coating by precision etching to reveal the transparent material inner portion.

Further, to allow high resolution between the transparent markings of the multi-purpose object and adjacent areas to the transparent markings, the multi-purpose object may in an embodiment be configured with a second coating that is configured as a light-opaque coating, wherein the light-opaque coating is covering the one or more surfaces of at least the first section in areas different from positions of said transparent markings.

This second light-opaque coating can be applied to the exterior of the first light-reflective coating (i.e. to ensure that the transparent markings can be lit up from the inside of the multi-purpose object), and the known pattern of calibration markings (i.e. transparent markings) is removed from both the first light-reflective coating and the second light-opaque coating by precision etching to reveal the transparent material inner portion. In this way, the first and second section is coated with a light-reflective coating, wherein subsequently a light-opaque coating is applied to at least a surface of the first sections, so that a high contrast between the light-opaque areas and the transparent markings of the multi-purpose object can be achieved, while allowing the internal parts of the first and second section to be light-reflective.

It should be noted that in an embodiment, the first reflective coat may be opaque, allowing the transparent markings to emit light. In such embodiment, only the opaque coating of first and second section is necessary for providing the adequate contrast to the emitted light from the transparent markings. In an alternative embodiment, the outer portion may be an opaque outer rigid portion, for example an aluminium or other suitable rigid box, and the known pattern of calibration markings and/or positioning markings are created by removing the opaque outer rigid portion by precision machining to expose the transparent material inner portion.

In a further embodiment, the object, in which the opaque outer rigid portion includes an inner surface, a first light-reflective coating is applied to the inner surface to substantially reflect light incident in the internal space from a light source so as to illuminate the object.

Since both methods use precision machining to remove the opaque coating or rigid outer portion, the resulting calibration markings are more accurate and far cheaper than the conventional screen printing used to create calibration markings on the surface of a conventional metal calibration sheet.

A laser lighting system can be used to illuminate the object by aligning the planes of laser light generated by the laser lighting system with positioning markings on the exterior of the calibration object where part of the outer portion is removed to reveal the transparent inner portion. Such positioning marking can be of the form of a transparent horizontal and/or vertical slot. Such positioning marking facilitate accurate positioning of the calibration object.

By identifying the position of brightest illumination, either visually, by imaging, or by using a light meter within the object or externally as part of the treatment apparatus, the initial positioning of the calibration object for obtaining radiation images of the radio-opaque targets and for determining camera positions and intrinsic camera parameters can be obtained with higher accuracy when compared to the known method of positioning the calibration object which relies on visual alignment of the laser light with the positioning markings rather than the illumination of the object. Thus, in an embodiment, the multi-purpose object comprises a light meter housed within said first and/or second section.

In addition to the positioning markings enabling the calibration object to be positioned at the treatment apparatus iso-center, the position markings also allow light from the external light source, such as the laser lighting system, or an LED light source, to enter into the internal space of the calibration object and illuminate the calibration markings to enable highly accurate imaging.

In one embodiment, the coating comprises a first light-reflective coating applied to the transparent material inner portion to substantially reflect light incident in the internal space from a light source so as to illuminate the calibration object and a second light-opaque coating applied to the first light-reflective coating, the light-opaque coating advantageously providing a contrast with the transparent inner material portion of the calibration object for subsequent imaging.

In other words, in an embodiment, the object may comprise an internal light source positioned within or adjacent to the first and/or second section, said light source being operable to illuminate internal parts of said first and/or second section, when said object is imaged by a camera system of said patient tracking system. That is to say that the internal light source may be positioned in or adjacent the internal space, the light source being operable to illuminate the transparent material inner portion when the calibration object is being imaged by a camera system of a patient monitoring system.

The internal light source may further comprise a receiver, which can be activated upon receiving a signal from the camera system of the patient monitoring system when the calibration markings are imaged by the camera system, or when a proximity or pressure sensor detects the calibration object is positioned on a mechanical couch of the patient monitoring system. This ensures the object is only illuminated when required, that is, when calibration images are obtained. Alternatively, a manual switch can be provided on the object to activate the internal light.

The calibration object can also include a light meter to measure the level of illumination of the object caused by an external light source such as a laser lighting system. Whilst the level of illumination can be judged visually, the light meter ensures highly accurate light quantity measurements can be obtained to enable both accurate position of the calibration object and verification of the accuracy of the laser lighting system by comparing the measured light quantity with stored reference light quantity values. In alternative embodiments, the light meter can be remote from the calibration object in the treatment room.

When calibrating the laser lighting system, a cover can be provided to ensure light from the laser lighting system only enters the calibration object through one of the positioning markings to ensure consistency in the comparison with the reference light value. The calibration of the laser lighting system in view of estimating the accuracy of the laser lighting system is explained in further detailed throughout the disclosure.

In more details, the second section is configured so that at least one radio-opaque target is provided in the internal space in a known position relative to an exterior surface of the calibration object.

In an embodiment, each of the target objects is positioned in the same horizontal plane within recesses(s) of the second section.

To ensure that none of the target objects do not cast a shadow over each other, the multi-purpose object (such as calibration object) may in an embodiment be configured such that a plurality of sides of the second sections includes at least two sides arranged perpendicularly to each other, in which each of the plurality of radio-opaque targets are arranged relative to each other such that none of the radio-opaque targets casts a shadow over any of the other of the radio-opaque targets in the horizontal plane when viewed from the each of the at least two sides.

In use, the multi-purpose object is e.g. applied in a method of calibrating and/or monitoring a patient treatment system comprising one or more image detectors, the method including the steps of:

providing a multi-purpose object to the embodiments described herein;

positioning said object in a patient treatment system;

illuminating the object when the object is positioned in the patient treatment system, wherein the transparent markings are lit up by the illumination;

imaging the object to obtain a pattern image created from the illuminated transparent markings on the object. Further details of the use of the multi-purpose object will be described in the following.

BRIEF DESCRIPTION OF THE DRAWINGS

Embodiments of the present invention will now be described in greater detail with reference to the accompanying drawings in which.

SPECIFIC EMBODIMENTS

Prior to describing a multi-use calibration object in accordance with the present invention, an exemplary patient monitoring system and radiotherapy treatment apparatus which can be calibrated using the described method will first be described with reference to FIGS. 1-3. Furthermore, it should be understood that the multi-use calibration object is contemplated as a multi-purpose object that can be used for calibration and/or monitoring and/or tracking of components and/or patients in a treatment room setup, such as in a radiotherapy treatment room, a CT or MR scanning room etc.

Figure 1:
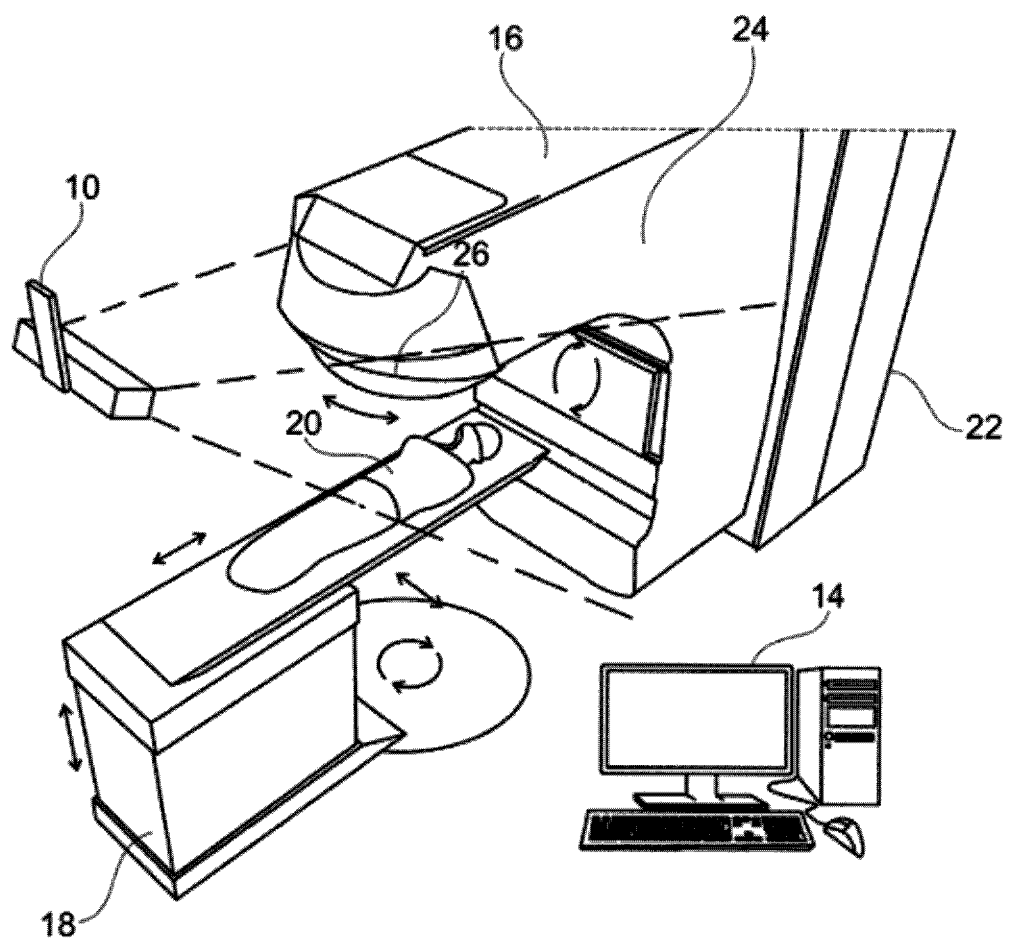
FIG. 1 is a schematic perspective view of an exemplary treatment apparatus and a patient monitor.

FIG. 1 is a schematic perspective view of an exemplary patient monitoring system comprising a camera system comprising a number of cameras mounted within a number of camera pods 10 one of which is shown in FIG. 1 that are connected by wiring (not shown) to a computer 14. The computer 14 is also connected to treatment apparatus 16 such as a linear accelerator for applying radiotherapy. A mechanical couch 18 is provided as part of the treatment apparatus upon which a patient 20 lies during treatment. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

The treatment apparatus 16 comprises a main body 22 from which extends a gantry 24. A collimator 26 is provided at the end of the gantry 24 remote from the main body 22 of the treatment apparatus 16. To vary the angles at which radiation irradiates a patient 20, the gantry 24, under the control of the computer 14, is arranged to rotate about an axis passing through the center of the main body 22 of the treatment apparatus 16 as indicated on the figure. Additionally, the direction of irradiation by the treatment apparatus may also be varied by rotating the collimator 26 at the end of the gantry 24 as also indicated by the arrows on the figure.

To obtain a reasonable field of view in a patient monitoring system, camera pods 10 containing cameras monitoring a patient 20, typically view a patient 20 from a distance (e.g. 1 to 2 meters from the patient being monitored). In the exemplary illustration of FIG. 1, the field of view of the camera pod 10 shown in FIG. 1 is indicated by the dashed lines extending away from the camera pod 10.

As is shown in FIG. 1, typically such camera pods 10 are suspended from the ceiling of a treatment room and are located away from the gantry 24 so that the camera pods 10 do not interfere with the rotation of the gantry 24. In some systems, a camera system including only a single camera pod 10 is utilized. However, in other systems, it is preferable for the camera system to include multiple camera pods 10 as rotation of the gantry 24 may block the view of a patient 20 in whole or in part when the gantry 24 or the mechanical couch 18 are in particular orientations. The provision of multiple camera pods 10 also facilitates imaging a patient from multiple directions which may increase the accuracy of the system.

A laser lighting system (not shown), typically in the form of a set of laser lights arranged to generate three planes of laser light may be provided to highlight the treatment room iso-center, being the position in the treatment room, through which the treatment apparatus 16 is arranged to direct radiation regardless of the orientation and position of the collimator 26 and gantry 24. When a patient 20 is positioned for treatment, this treatment room iso-center should coincide with the tissue intended to receive the greatest amount of radiation.

Figure 2:
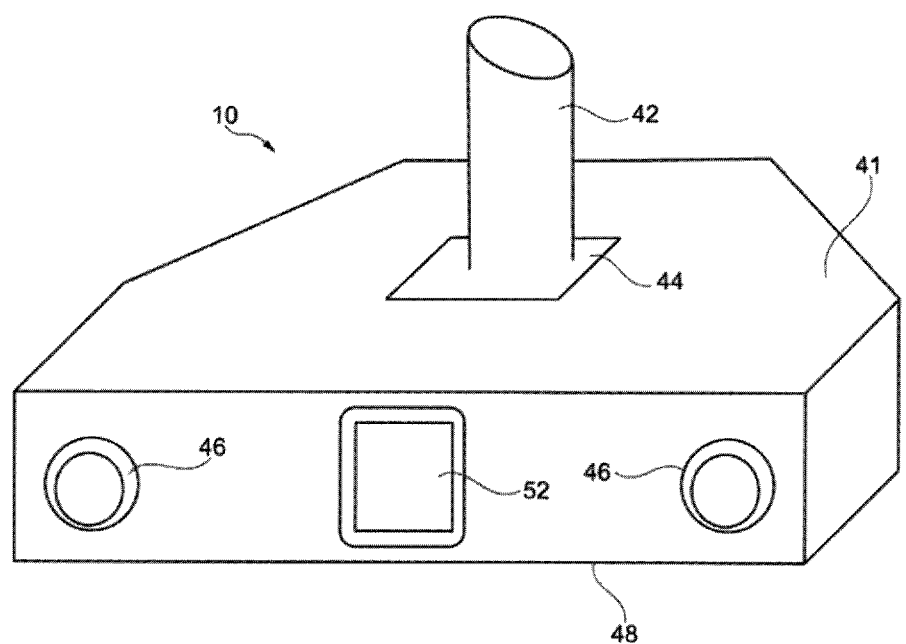
FIG. 2 is a front perspective view of a camera pod of the patient monitor of FIG. 1.

FIG. 2 is a front perspective view of an exemplary camera pod 10.

The camera pod 10 in this example comprises a housing 41 which is connected to a bracket 42 via a hinge 44. The bracket 42 enables the camera pod 10 to be attached in a fixed location to the ceiling of a treatment room whilst the hinge 44 permits the orientation of the camera pod 10 to be orientated relative to the bracket 42 so that the camera pod 10 can be arranged to view a patient 20 on a mechanical couch 18. In this embodiment in which the 3D camera system 10 is a stereoscopic camera system, a pair of lenses 46 are mounted at either end of the front surface 48 of the housing 41. These lenses 46 are positioned in front of image capture devices/cameras such as CMOS active pixel sensors or charge coupled devices (not shown) contained within the housing 41. The cameras/image detectors are arranged behind the lenses 46 so as to capture images of a patient 20 via the lenses 46.

In this example, a speckle projector 52 is provided in the middle of the front surface 48 of the housing 41 between the two lenses 46 in the camera pod 10 shown in FIG. 2. The speckle projector 52 in this example is arranged to illuminate a patient 20 with a non-repeating speckled pattern of red light so that when images of a patient 20 are captured by the two image detectors mounted within a camera pod 10 corresponding to portions of captured images can be more easily distinguished. To that end the speckle projector comprises a light source such as a LED and a film with a random speckle pattern printed on the film. In use light from the light source is projected via the film and as a result a pattern consisting of light and dark areas is projected onto the surface of a patient 20.

In some monitoring systems, the speckle projector 52 could be replaced with a projector arranged to project structured light (e.g. laser light) in the form of a line or a grid pattern onto the surface of a patient 20 or alternatively a time of flight camera could be utilized in which a projector projects a pattern of light onto the surface and the timing of the reflection of the light is utilized to determine the distance between the surface and a camera. In such systems, rather than providing two cameras, a single camera might be utilized.

Figure 3:
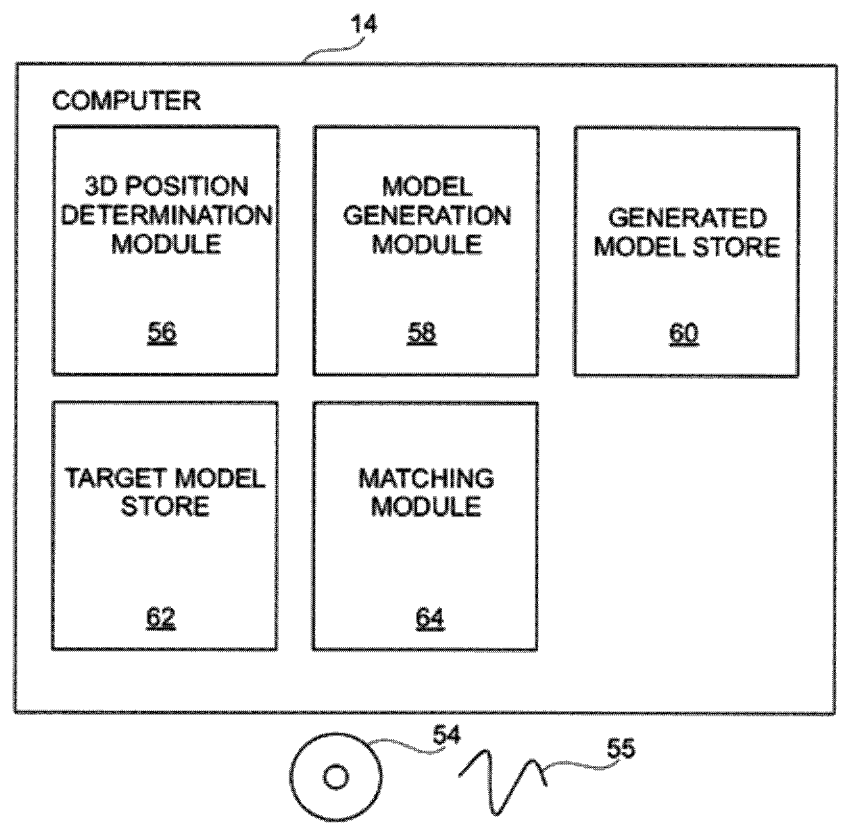
FIG. 3 is a schematic block diagram of the computer system of the patient monitor of FIG. 1.

FIG. 3 is a schematic block diagram of the computer 14 of the patient monitor of FIG. 1. In order for the computer 14 to process images received from the camera pods 10, the computer 14 is configured by software either provided on a disk 54 or by receiving an electrical signal 55 via a communications network into a number of functional modules 56-64. In this example, the functional modules 56-64 comprise: a 3D position determination module 56 for processing images received from the 3D camera system 10, a model generation module 58 for processing data generated by the 3D position determination module 56 and converting the data into a 3D wire mesh model of an imaged surface; a generated model store 60 for storing a 3D wire mesh model of an imaged surface; a target model store 62 for storing a previously generated 3D wire mesh model; and a matching module 64 for determining rotations and translations required to match a generated model with a target model.

In use, as images are obtained by the image capture devices/cameras of the camera pods 10, these images are processed by the 3D position determination module 56. This processing enables the 3D position determination module to identify 3D positions of corresponding points in pairs of images on the surface of a patient 20. In the exemplary system, this is achieved by the 3D position determination module 56 identifying corresponding points in pairs of images obtained by the camera pods 10 and then determining 3D positions for those points based on the relative positions of corresponding points in obtained pairs of images and stored camera parameters for each of the image capture devices/cameras of the camera pods 10. In other embodiments such as monitoring systems based on the projection of structured light or time of flight cameras the 3D position determination module 56 is modified so as to process images and determine 3D position data based on the appearance of a pattern of structured light in obtained images or the timing of the receipt of a reflection of a pattern of light.

The position data generated by the 3D position determination module 56 is then passed to the model generation module 58 which processes the position data to generate a 3D wire mesh model of the surface of a patient 20 imaged by the camera pods 10. The 3D model comprises a triangulated wire mesh model where the vertices of the model correspond to the 3D positions determined by the 3D position determination module 56. When such a model has been determined it is stored in the generated model store 60.

When a wire mesh model of the surface of a patient 20 has been stored, the matching module 64 is then invoked to determine a matching translation and rotation between the generated model based on the current images being obtained by the camera pods 10 and a previously generated model surface of the patient stored in the target model store 62. The determined translation and rotation can then be sent as instructions to the mechanical couch 18 to cause the couch to position the patient 20 in the same position relative to the treatment apparatus 16 as the patient 20 was in when the patient 20 was previously treated.

Subsequently, the image capture devices/cameras of the camera pods 10 can continue to monitor the patient 20 and any variation in position can be identified by generating further model surfaces and comparing those generated surfaces with the target model stored in the target model store 62. If it is determined that a patient 20 has moved out of position, the treatment apparatus 16 can be halted or a warning can be triggered and the patient 20 repositioned, thereby avoiding irradiating the wrong parts of the patient 20.

Referring to FIGS. 4 to 11, a novel multi-use (i.e. multi-purpose) calibration object 100 for calibrating a patient monitoring system such as the above will now be described. As previously mentioned the multi-purpose object can also be used in e.g. tracking and monitoring of for example a couch movement in a CT scanning system and or e.g. a MR scanning system.

It should be noted that in the following, the multi-purpose object will mainly be described in the use of a calibration and monitoring object, but this should be contemplated not to exclude other uses, such as tracking movement of a couch in a CT or e.g. MR scanning system.

Additionally, it should be noted that in the following, the object will be described to comprise a first section denoted as a lid and a second section denoted as a base section of the object.

Figure 4:
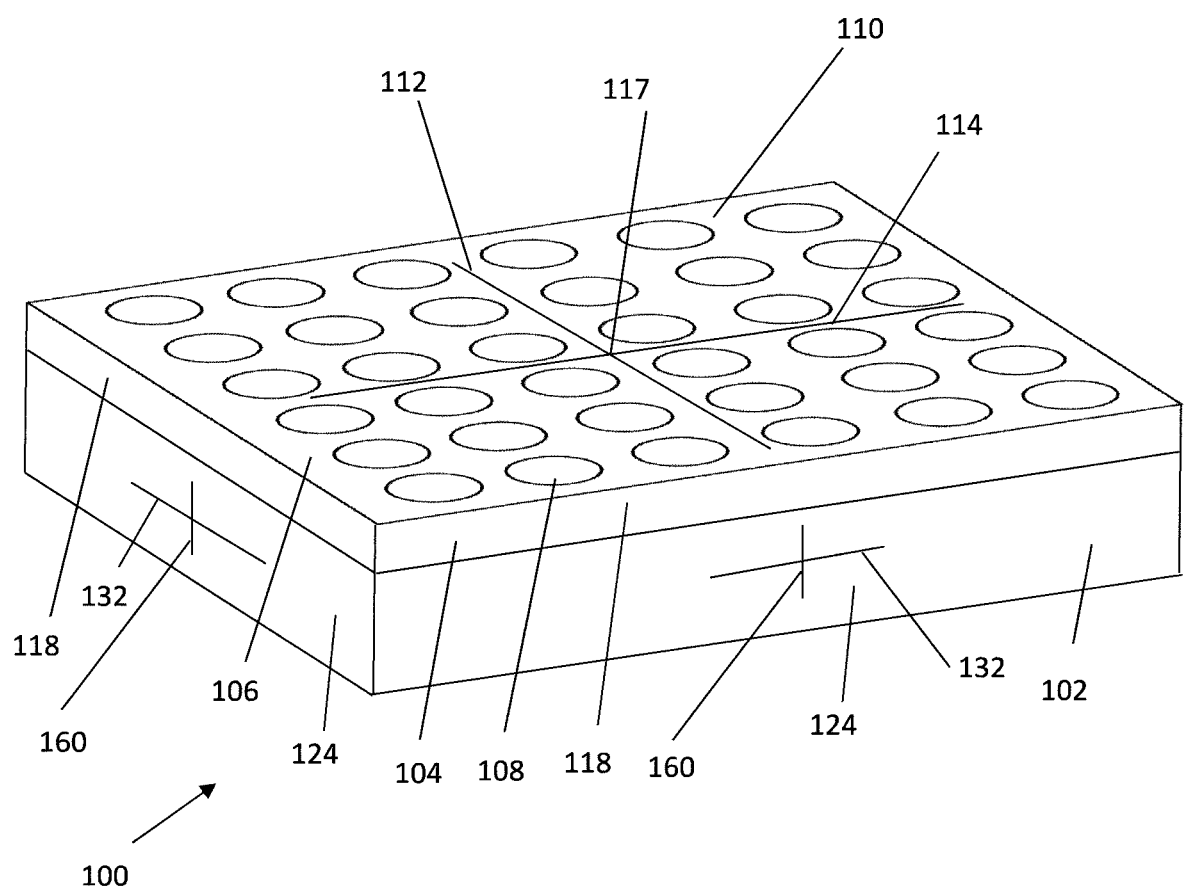
FIG. 4 is a perspective view of an assembled calibration object in accordance with one aspect of the present invention.

As is shown in FIG. 4, the calibration object 100 comprises a base section 102 and a lid section 104. Prior to assembly, both the base section 102 and lid section 104 have the same square plan-profile which in this exemplified embodiment is 120 mm square, although it will be appreciated in other embodiments other sizes and shapes can be used. The lid section 104 in this exemplified embodiment has a thickness of 3.7 mm and the base section 102 has a thickness of 11.3 mm.

Both the base section 102 and the lid section 104 are made from a low-density transparent plastic material such as polystyrene. In other embodiments, alternative materials could be used, the important requirement being that the assembled calibration object 100 preferably is rigid, and the material used to from the base section 102 and lid section 104 preferably allows the transmission of radiation and light from a source such as a laser or LED light, the reasons for which will be described below.

Figure 5:
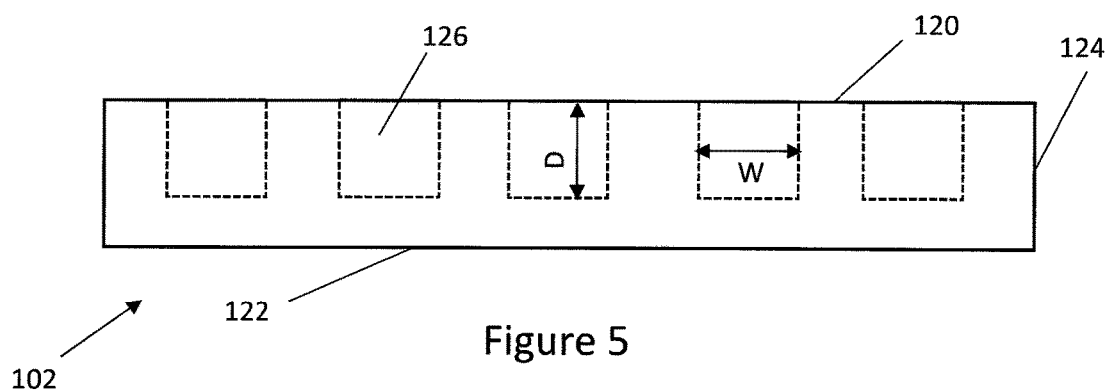
FIG. 5 is a side view of the base section of the calibration object of FIG. 4 before the radio-opaque targets have been inserted.
Figure 6:
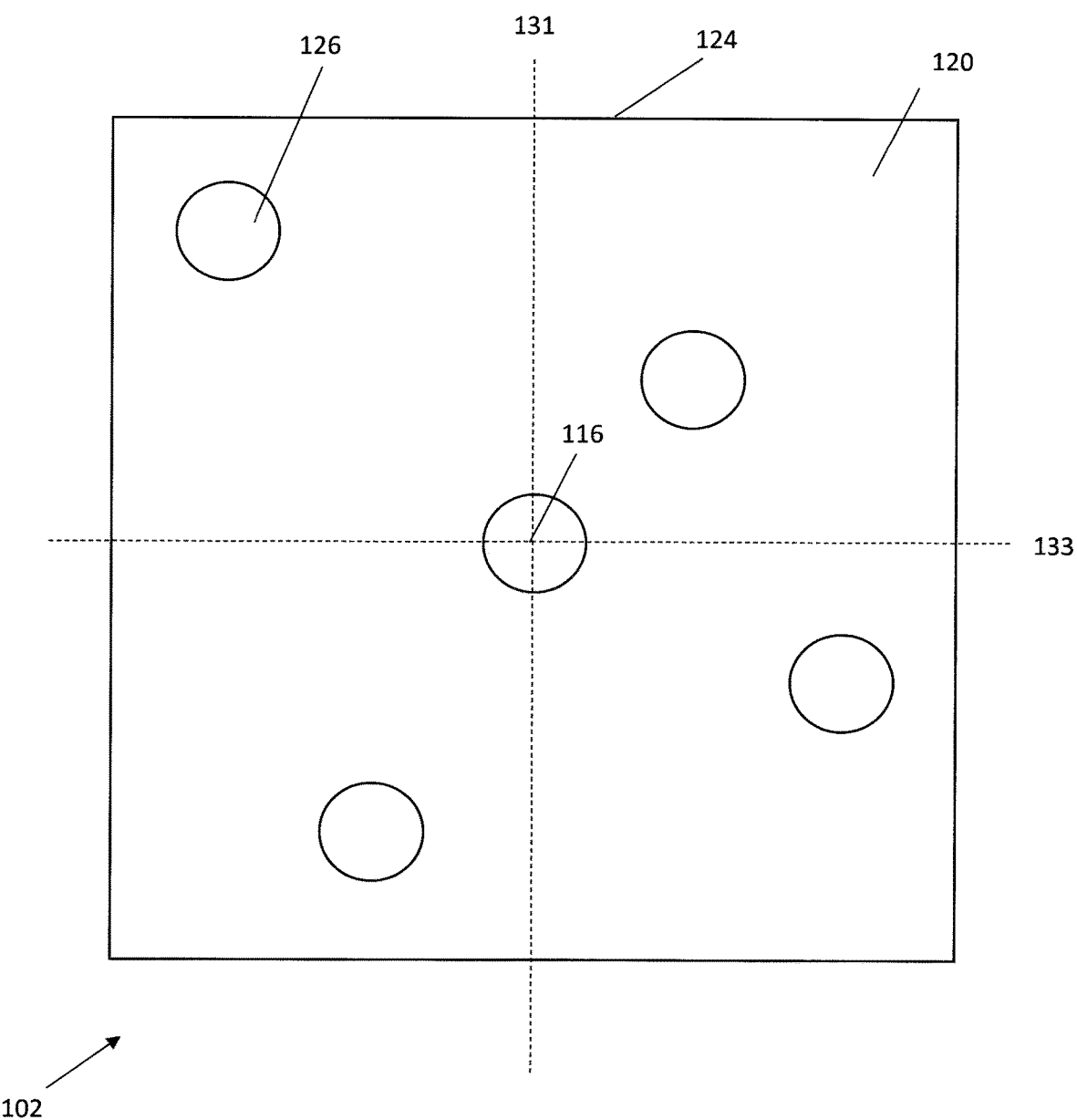
FIG. 6 is a plan view of the base section of the calibration object of FIG. 4.

As can be seen more clearly in FIGS. 5 and 6, which are a side and plan view of the base section 102 respectively, the base section 102 has a top face 120, bottom face 122 and four side faces 124. Five cylindrical recesses 126 are precision machined into the base section 102, each of the cylindrical recesses 126 having an identical depth D and width W. Thus, the base section (i.e. the second) comprises one or more recess(es) 126 configured with a depth and a width, wherein each of the one or more recess(es) 126 is configured to contain a target objects, as will be explained in the following. Furthermore, as will become apparent throughout the description, the second section if configured to be connected with the first section (e.g. a lid).

Figure 7:
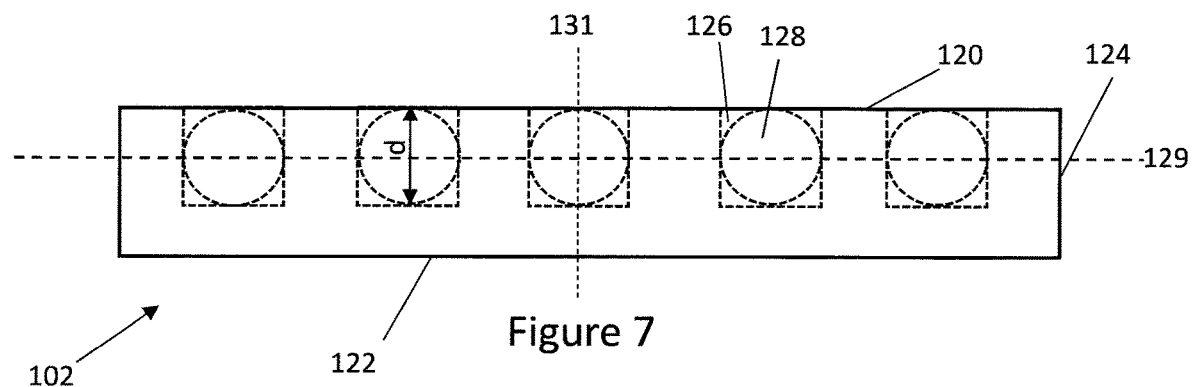
FIG. 7 is a side view of the base section of FIG. 6 with the radio-opaque targets inserted.

As shown in FIG. 7, a radio-opaque target (i.e. a target object) or sphere 128, having a diameter d is inserted into each of the recesses 126, the diameter d of the sphere enabling a tightly tolerance fit between each sphere 128 and the recess 126 into which it is housed. It will be understood that since the recesses 126 are of identical depth D, the spheres 128, once housed within each of the recesses 126, all lie in the same horizontal plane 129.

Figure 9:
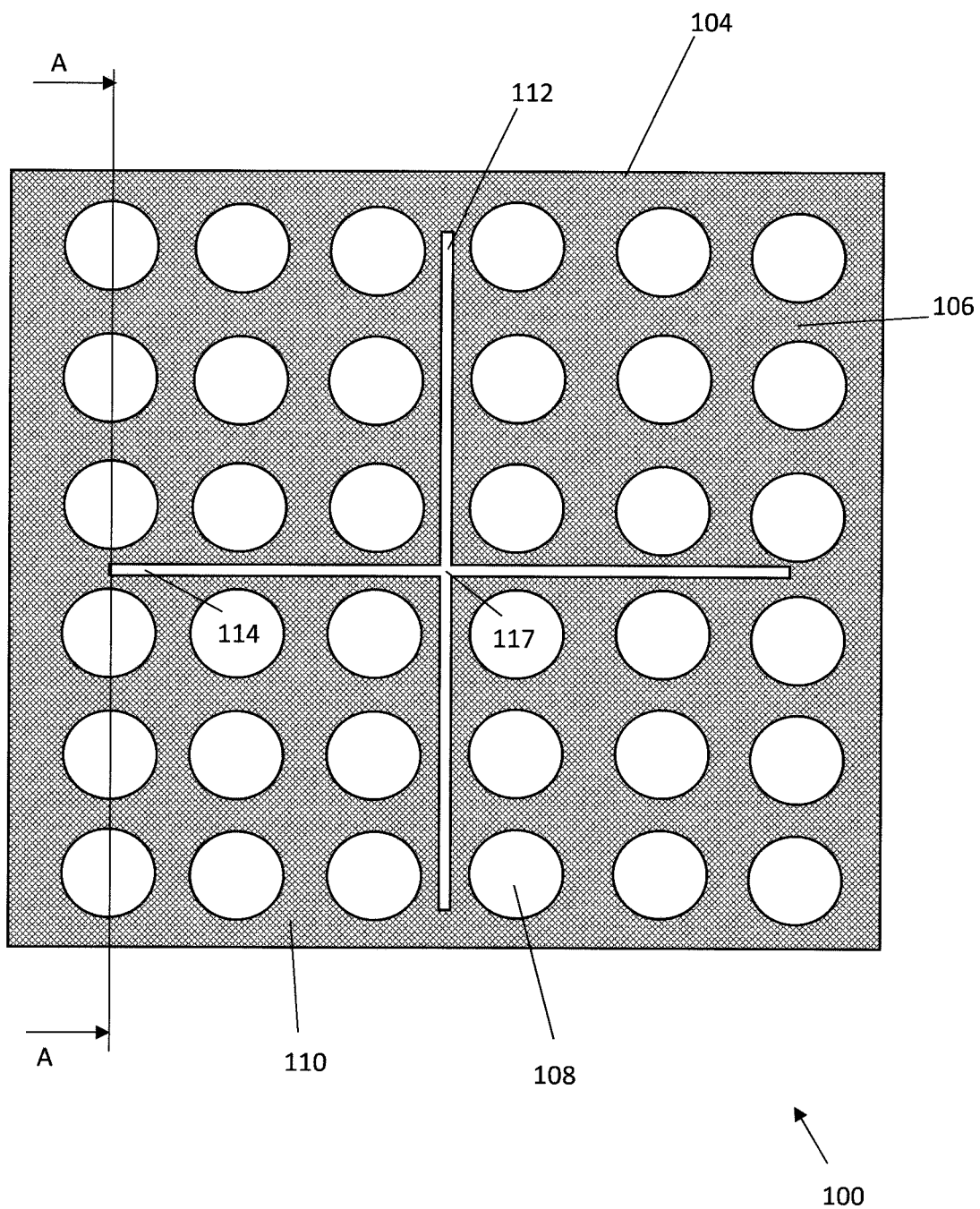
FIG. 9 is a plan view of the coated calibration object of FIG. 4 after etching to reveal the calibration markings.

As is illustrated in FIG. 6, one of the cylindrical recesses 126 is positioned at a center-point 116 of the base section 102 defined by the intersection of vertical planes 131,133, and coinciding, once assembled, with a center-point 117 of the lid section 104 (FIG. 9). The remaining four cylindrical recesses 126 are positioned such that, when the radio-opaque spheres 128 are inserted into each recess 126, none of the spheres cast a shadow over any of the other spheres when viewed perpendicularly from the side surfaces 124 (best seen in FIG. 6).

It will also be understood that by precision machining the cylindrical recesses 126 within which the spheres 128 are housed, the position of the spheres 128 relative to the exterior of the calibration object can be known to a very high degree of accuracy.

Figure 8:
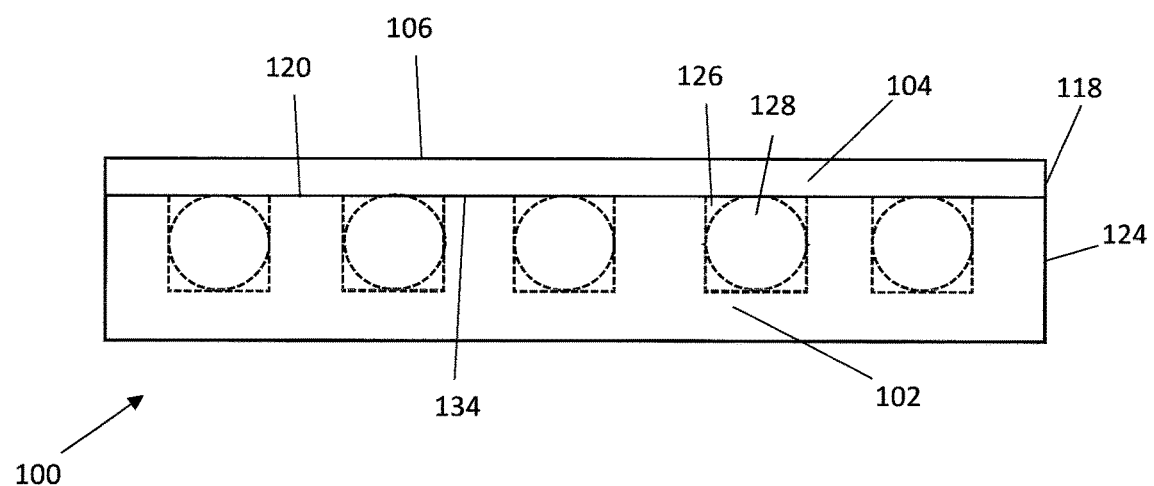
FIG. 8 is a side view of the base section of FIG. 5 with the radio-opaque targets inserted and the lid section secured.

Referring to FIGS. 4 and 8, the lid section 104 (also contemplated as the first section) has an upper surface 106, a lower surface 134 and four side faces 118.

With the spheres 128 housed within the recesses 126, the lower surface 134 of the lid section 104 is positioned on, and secured to, the top face 120 of the base section 102 (FIG. 8) using screws (not shown), or any other suitable fixing means, for example, using an adhesive.

Furthermore, the lid (i.e. the first section) is provided with a plurality of transparent markings 108. The multi-purpose object is configured such that one or more of a surface of the base and/or the lid section comprise a coating, wherein at least one coating material is covering the one or more surfaces at areas different from positions of said transparent markings. In more detail, the coating material covering at least areas at positions of said transparent markings, is configured as a first light-reflective coating having the properties of reflecting light incident on an internal space of said first and/or second section.

Furthermore, a second light-opaque coating is covering one or more surfaces of at least the first section in areas different from positions of said transparent marking. Thus, the multi-purpose object comprises a first and a second coating, where the first coating at least covers the transparent markings, to ensure that these a light reflective, and a second coating is light opaque ensuring that areas different from the transparent markings do not allow light to enter. In this way, when illuminating the multi-purpose object a high contrast is created between the light opaque and light-reflective areas of the surface of at least the lid.

In more detail, the pattern of calibration markings and positioning markings (i.e. the transparent markings) are created on the assembled calibration object 100 as follows:

A first light-colored reflective coating, for example, a white paint 130, of a thickness of approximately 1 mm, is applied to all surfaces of the calibration object 100, that is, the bottom face 122 and the side faces 124 of the base section 102, and the upper surface 106 and side faces 118 of the lid section 104. A second dark-colored coating, for example, a black paint 110, of a thickness of approximately 1 mm, is then applied over all of the white paint 130.

Calibration markings are then created by etching portions from and through the entire black paint 110 and white paint 130 thicknesses of the upper surface 106 of the lid section 104 using a precision machining process, that is, a computer-controlled machining process which can remove material from a workpiece to tight dimensional tolerances. The computer is programmed to remove portions in the form of a 6×6 grid of identical cylindrical recesses 108 of known diameter and position relative to each other, to reveal the transparent upper surface 106 of the lid section 104 below. The same machining process is then used to reveal etched slots 112,114 from the upper surface 106 of the lid section 104. The slots intersect the center-point 117 of the lid section 104.

Figure 10:
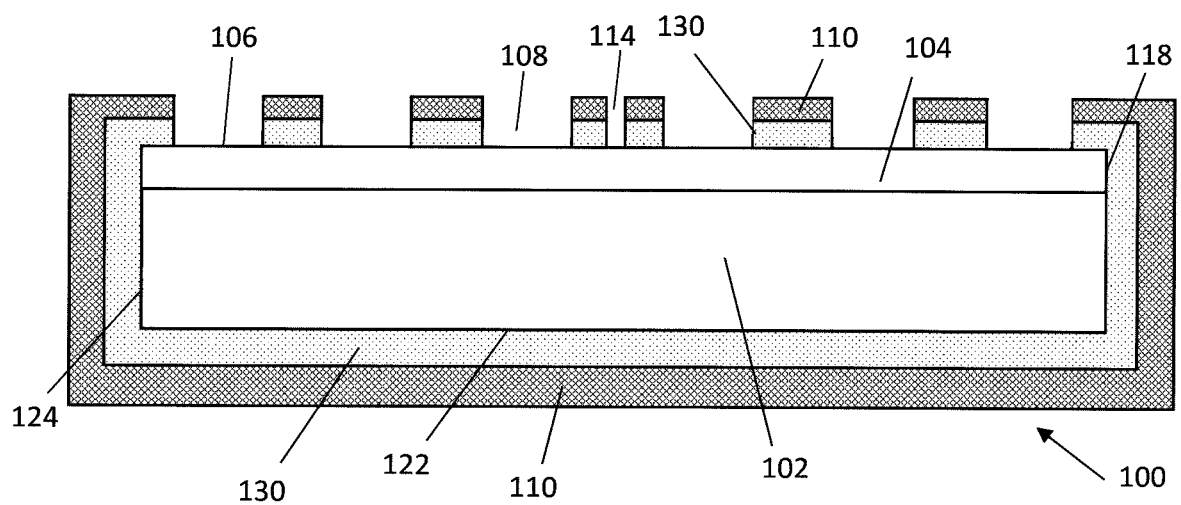
FIG. 10 is a schematic side sectional view through A-A of the coated calibration object of FIG. 4 after etching to reveal the calibration markings.

The grid of cylindrical recesses 108 and slots 112,114 can be clearly identified in the plan view of the calibration object 100 in FIG. 9. FIG. 10 shows the white coating 130 having been partially removed. In FIG. 10, the thicknesses of the black paint 110 and the white paint 130 relative to the height of the lid 102 and base 104 sections are exaggerated to illustrate how the paint 110,130 is applied and subsequently removed.

The revealed transparent recesses 108 and etched slots 112,114 contrast in color when compared to the remaining black paint 110 on the upper surface 106 (best seen in FIG. 9). By coating the upper surface 106 in this way, and then removing portions of the coating by etching, the recesses 108 and slots 112,114 can be rendered onto the surface 106 of the calibration object 100 with very high accuracy in a manner which is far cheaper to produce than the conventional screen printing used to create a pattern on the surface of a conventional metal calibration sheet. It is the revealed or exposed cylindrical recesses 108 on the lid section 104 that are used as the calibration markings for subsequent determination of the internal camera characteristics for each of the cameras in the monitoring system as will be described below.

The same precision machining process used to reveal the grid of cylindrical recesses 108 and etched slots 112,114 is used to create a horizontal slot 132 of height 1 mm and a vertical slot 160 of width 1 mm that is perpendicular to the horizontal slot 132, in two adjacent side faces 124 of the base section 102 by etching the thickness of the combined black 110 and white 130 paint from the adjacent side faces 124 of the base section 102 to reveal the transparent material of the base section 102. The horizontal and vertical slots 132,160 are positioned such they lie in the same plane as planes 129,131 or 133 respectively (FIGS. 4, 6 and 7).

It will be understood that the white paint 130 reflects any light inside the calibration object 100. When used in combination with an external light source, the slots 132,160 act as positioning markings by enabling light from that light source to enter inside the calibration object and assist in positioning the calibration object as will be described below.

It will further be appreciated that with the calibration object 100 being made of a transparent material and the paint on the calibration object having been etched away to reveal the recesses 108, and slots 112,114, the interior of the calibration object 100 can be illuminated either by using the external light source or providing an internal light source positioned inside the calibration object so as to cause the pattern of recesses 108 and slots 112,114 to be illuminated internally, or back-illuminated, and stand out against or contrast with the black paint on the upper surface 106 of the calibration object. This back-illumination is assisted by the presence of the white paint 130 (or alternatively other light colored coating) on the remaining other surfaces of the calibration object 100 as light will be reflected off the white on the bottom face 122 and side faces 118,124.

In the above described calibration object 100, the assembled lid 104 and base 102 sections can be considered a transparent material inner portion, and the black 110 and white 130 paint, an outer portion which substantially covers (prior to etching of the paint to reveal calibration and positioning markings) the transparent material inner portion.

In alternative embodiments, the bottom face 122 and the side faces 124 of the base section 102 can be masked-off when the black paint 110 is applied to the calibration object 100 to prevent the white paint 130 on the base section from being over-painted with the black paint 110. Such an embodiment has the advantage that as most of the white paint is not overpainted there is less opportunity for the white paint to become contaminated with the black paint which may reduce the reflectivity of the painted white surface. Alternatively, the calibration object could be coated with only white paint without the layer of black paint being applied.

In use, the multi-purpose object is preferably used in a radio treatment room setup, but other imaging modalities, such as CT or MR scanning could be contemplated. In at least a radiotherapy treatment setup for monitoring of a patient, the multi-purpose object is used as follows:

In a treatment room having one or more image detectors the multi-purpose object according to the disclosure is positioned on e.g. a couch in the treatment room. Afterwards the, object is illuminated by e.g. a laser or other light source, whereby the transparent markings of the object are lit up by said illumination. In a subsequent step, the object is imaged to obtain an image of the pattern (i.e. a pattern image) created via said illuminated transparent markings on said object. This "pattern image" is used to ensure that intrinsic and extrinsic parameters of the cameras are correctly calibrated to the treatment room. The pattern image is obtained due to the fact that the multi-purpose object comprises a high contrast between the transparent markings and the light-opaque areas of the surface of the first section.

In a subsequent step, the multi-purpose object is at the same time used to estimate the location of the iso-center in a radiotherapy treatment setup. Thus, in a further step the multi-purpose object is further configured to be positioned substantially at an iso-center of the patient treatment system; wherein further steps includes: a subsequent irradiating of the multi-purpose object; obtaining irradiated images of said multi-purpose object; and determining the relative location of said targets within the multi-purpose object by analysing said irradiated images of said object. It should be noted that these steps, could be done at the same time (i.e. without re-positioning of the multi-purpose object for each step).

The irradiated images and the pattern images are utilized as input to a model generator, wherein the model generator is configured to utilise the pattern images to determine a positioning of a set of image detectors and a set of intrinsic parameters of the camera system and to utilise the irradiated images to process the irradiated images to determine the location of a treatment room iso-center.

In a more detailed exemplified explanation, in use, in this embodiment, the calibration object 100 is placed on the surface of the mechanical couch 18 using the laser lighting system. The position and orientation of the calibration object 100 is then adjusted so that the lines 112,114 on the exterior of the calibration object are visibly aligned with the planes of laser light projected by a treatment room laser lighting system to initially position the calibration object.

In such an orientation, the center point 117 of the calibration object 100 should be located co-incident with the point in space highlighted by the laser lighting system.

Figure 11:
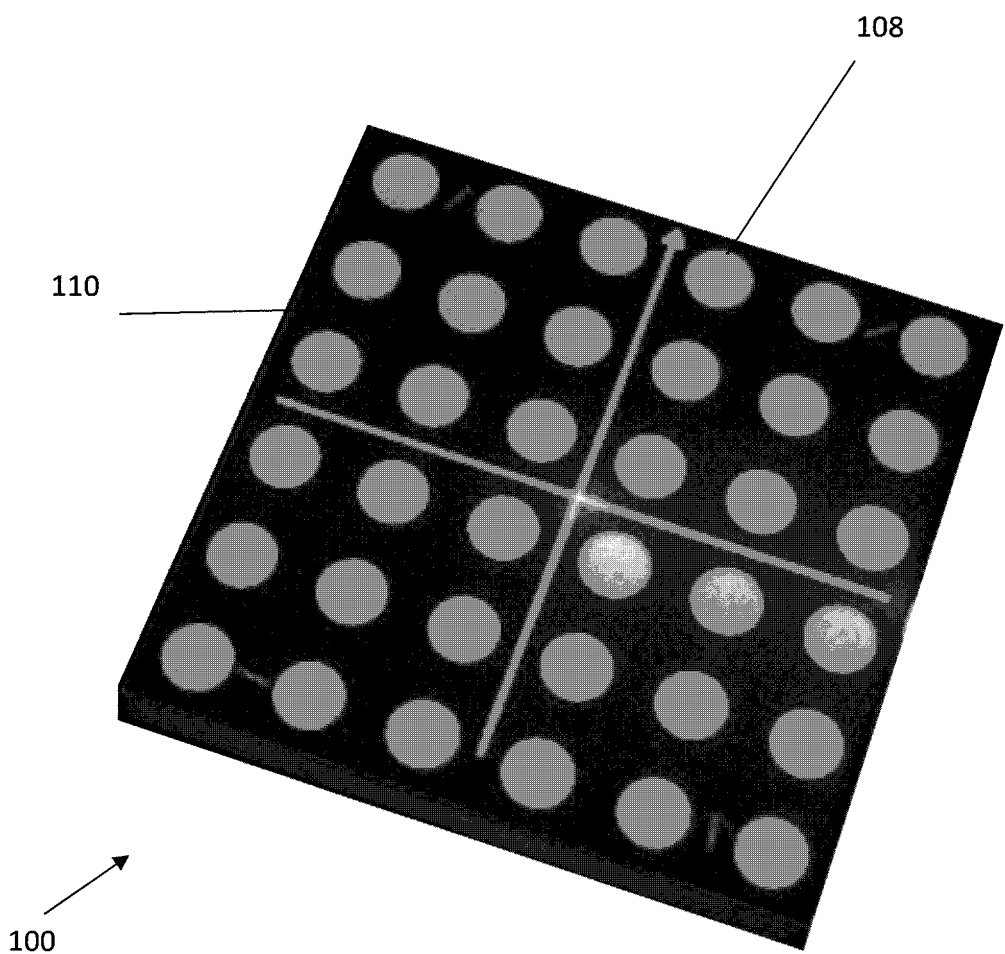
FIG. 11 is an image of the calibration object of FIG. 4 illuminated by a laser lighting system.

In addition, as laser light enters the calibration object 100 via the slots 132,160 and is reflected inside the object off of the white coating 130 on the bottom face 122 and side faces 118,124, the recesses 108 on the upper surface 106 will be back-illuminated by the reflected light creating a contrast with the black paint 110 on the upper surface 106 of the calibration object 100, providing a high contrast and high accuracy pattern which can be captured by the image detectors of the monitoring system (FIG. 11). This will also be the case in embodiments where the layer of black paint is omitted although the contrast will not be as great.

Once in position, a set of x-ray images of the calibration object 100 are then obtained. Typically, the images will be obtained by obtaining images of radiation projected from the treatment apparatus located at four specified angles (e.g. directly above, directly below, to the right, and to the left of the iso-center). The relative location of the center of the radio-opaque spheres 128 within the calibration object and the iso-center of the radio therapy treatment apparatus is then determined by analyzing radiographic images of the irradiation of the calibration object containing the irradiation targets.

More specifically, using conventional techniques such as are described in Low D A, Li Z, Drzymala R E. Minimization of target positioning error in accelerator-based radiosurgery. Med Phys. 1995; 22(4):443-48 and Grimm S L, Das I J, et al. A quality assurance method with sub-millimeter accuracy for stereotactic linear accelerators. J Appl Clin Med Phys. 2011; 12(1):182-98 and E Schriebmann, E Elder and T Fox, Automated Quality Assurance for Image-Guided Radiation Therapy, J Appl Clin Med Phys. 2009:10(1):71-79, the x-ray images can be processed to identify the relative location of the calibration object 100 and the treatment room iso-center. The model of the calibration object generated by the model generation module 58 can be utilized to identify the current position of the calibration object in model space and the two together can be utilized to identify the position of the treatment room iso-center in the model space of the system.

Images of the calibration object 100 are then obtained by the cameras of the monitoring system and processed to determine a set of internal camera characteristics for each of the cameras in the monitoring system. The images of the calibration object 100 obtained by the cameras are then processed to identify the locations of the circles (as defined by the transparent cylindrical recesses 108) appearing in the images and to determine a projective transformation to account for the surface being viewed at an oblique angle. A suitable transformation can then be applied to correct the image so as to generate a representation of the calibration object without that distortion. The relative locations of the circles as they appear in the corrected image and the extent to which they deviate from a regular grid can then be used to identify any lens irregularities present in the camera system and to relate distances in the images to real world distances.

In a stereoscopic camera based system, the projector 52 is then activated and images of light projected onto the surface of the calibration object 100 are captured by the monitoring system. The captured images are then processed by the 3D position determination module 56 and the model generation module 58 along with the captured x-ray images to determine the location of the calibration object 100 in model space. A comparison can then be made between the location of the center of the model of the calibration object 100 and a specific point in model space (typically the origin) and any measured difference between the center of the physical calibration object 100 and the identified location of the treatment room iso-center based on irradiating the calibration object 100. The co-ordinate system for the monitoring system can then be adjusted so as to locate the specific point in model space at the identified location of the iso-center and the monitoring system can then be utilized to monitor the positioning of a patient 20 relative to the identified location of the treatment room iso-center.

It will be appreciated that the above described approach to calibration of a patient monitoring system is not limited to the calibration of a stereoscopic camera based monitoring system. In particular it will be appreciated that in other monitoring systems such as systems based on time of flight or on the projection a pattern of laser light could equally be calibrated using the above approach. Furthermore, as previously mentioned it should be appreciated that the multi-purpose object could also be used in CT scanning setups as well as MR systems.

The described calibration object 100 has a number of advantages over conventional approaches to calibrating a patient monitoring system.

The described calibration object 100 can perform the functions of both the calibration sheet and the calibration cube conventionally required when calibrating a patient monitoring system. That is to say, in addition to providing an object having a high contrast pattern of calibration markings positioned relative to one another with very high accuracy enabling the positioning of image detectors of an imaging system and intrinsic parameters of such image detectors to be determined, the provision of a series of radio-opaque targets within the calibration object 100 also makes it suitable for use to determine the location of a treatment room iso-center by irradiating the object 100 and analyzing a radiation image of the radio-opaque targets.

The provision of the horizontal 132 and vertical slots 160 on the exterior of the calibration object 100 facilitates positioning the calibration object 100 with its center located at the assumed location of a treatment room iso-center (as highlighted by the treatment room laser lighting system) with high accuracy, as the illumination of the object will be brightest when the slots 132,160 on the exterior of the calibration object 132 are aligned with the planes of laser light generated by the laser lighting system. As such, the construction of the calibration object 100 facilitates high accuracy initial positioning of the calibration object 100 for obtaining radiation images of the radio-opaque targets and for determining camera positions and intrinsic camera parameters.

The accuracy with which a calibration object 100 is positioned could be enhanced by including a light meter within the calibration object 100 to provide a measurement of the levels of light received into the inside space of the calibration object 100. This also further facilitates using the calibration object 100 to perform a quality control check for the accuracy with which the laser lighting system identifies a treatment room iso-center which is described below.

Figure 12:
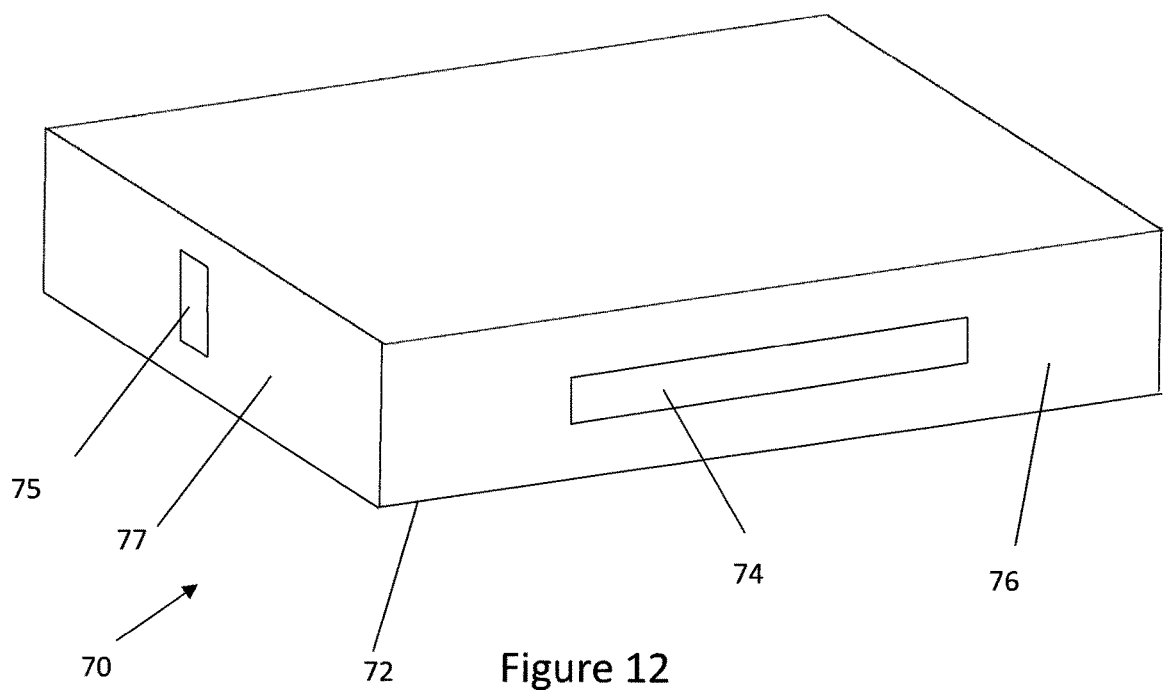
FIG. 12 is a perspective view of a cover for use with a calibration object to determine the accuracy of a laser lighting system.
Figure 13:
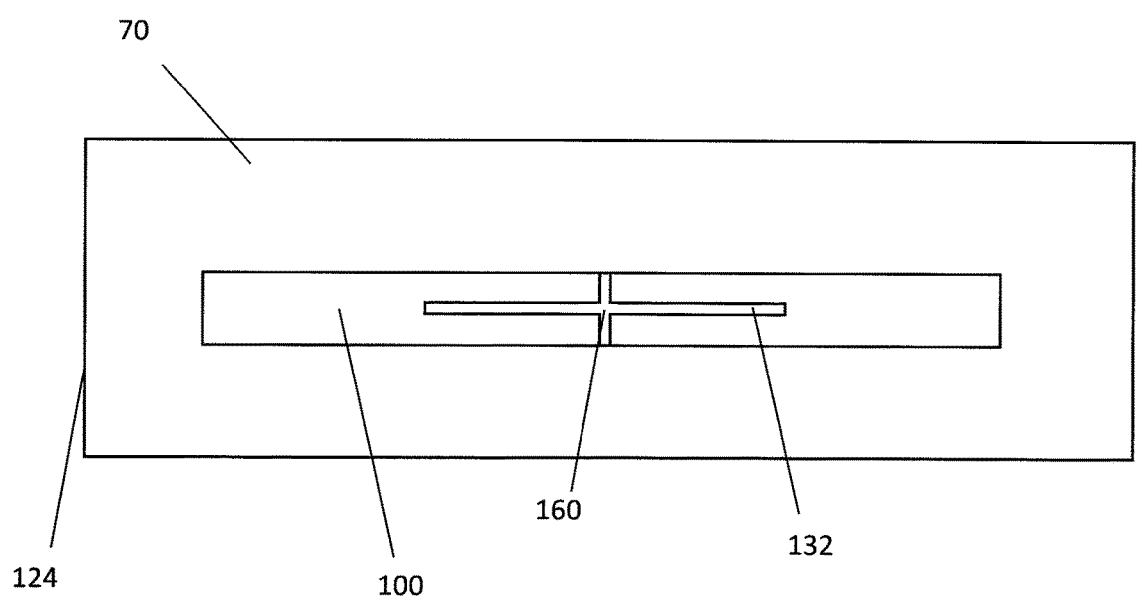
FIG. 13 is a side view of the cover of FIG. 12 positioned on the calibration object of FIG. 4.

Firstly, and following the methods described above using either radio-opaque spheres or imaging the calibration markings, the position of the iso-center of the treatment apparatus is determined. The object is then positioned at the iso-center, with this position confirmed using known methods of image analysis as described above. With the object in the known position, light from the laser lighting system is selectively allowed to enter the horizontal 132 or vertical 160 slots on only one of the side faces 124. This can be achieved by placing a cover 70 (FIGS. 12 and 13), which is the same shape as the calibration object 100 except slightly larger and having an open end 72 to enable it to be positioned onto and cover the calibration object 100.

The cover 70 has a retractable door 74 on one side face 76, which when retracted creates a horizontal opening which, with the cover positioned over the object 100, aligns with the horizontal slot 132 such that any light incident from the laser lighting system on the cover 70 will only enter the horizontal slot 132. The cover 70 has a further retractable door 75 on adjacent side face 77, which when retracted creates a vertical opening which, with the cover positioned over the object 100, aligns with the vertical slot 160 such that any light incident from the laser lighting system on the cover 70 will only enter the vertical slot 160. By incorporating horizontal and vertical openings on adjacent sides of the cover it is possible to align the horizontal laser light using the horizontal opening on the cover on one side, and the vertical laser light using the vertical opening on the cover on the adjacent side.

Alternatively, instead of using a cover to selectively block out the laser light so that it only enters one of the slots, the laser lighting system itself can be configured so that only one plane of light is activated.

With the object 100 positioned at the iso-center, and laser light entering one of the slots 132,160, a light meter (not shown) positioned within the calibration object 100 is used to measure the quantity of light received by the calibration object from the laser light. The quantity of light measured is then stored as the reference quantity of light that corresponds to the object being positioned at the treatment apparatus iso-center. This stored quantity of light can then be compared to future measurements of light quantity when the object is positioned at the iso-center. Any difference between the measured and stored light quantity can be attributed to either the object not being positioned at the iso-center, which can be confirmed by image analysis as described above, or, if the object is correctly positioned at the iso-center, to the inaccuracy of the laser lighting system. If the difference is attributable to the inaccuracy of the laser lighting system then the laser lighting system can be re-calibrated. The three laser lights planes of the laser system can be checked one light plane at a time, either by blocking the light using the cover 70 as described above, or by only activating one light, and measuring the quantity of light and comparing that quantity of light with the reference value for that light when the calibration object was correctly positioned at the iso-center.

It will be understood that either the laser light can be adjusted until the quantity of light measured corresponds to the reference quantity of light value, or the calibration object can be moved until the quantity of light measured corresponds to the reference quantity of light value. Both methods require the position of the treatment center iso-center to be determined in the usual known way, that is by imaging the calibration object and generating a model, or by irradiating the radio-opaque spheres, and then confirming that the calibration object is at the iso-center when the quantity of light measured corresponds to the reference quantity of light value. Any discrepancies will be due to errors in the laser lighting system as the iso-center will be known, as will the position of the calibration object relative to the iso-center.

It will also be understood that the slots 132,160 facilitate both positioning of the calibration object at the iso-center, as well as confirming the object is flat on the mechanical couch by comparing the measured light with the reference value, and verification of the accuracy of the laser lighting system.

Although in the above described embodiment, the positioning of the calibration object 100 has been described as utilizing the presence of slots 112,114,132,160 on the exterior of the calibration object 100 and aligning these with laser lights highlighting the estimated position of a treatment room iso-center, it will be appreciated that such slots are merely used to assist with the approximate positioning of the calibration object and some or all of the slots could potentially be omitted.

Figure 14:
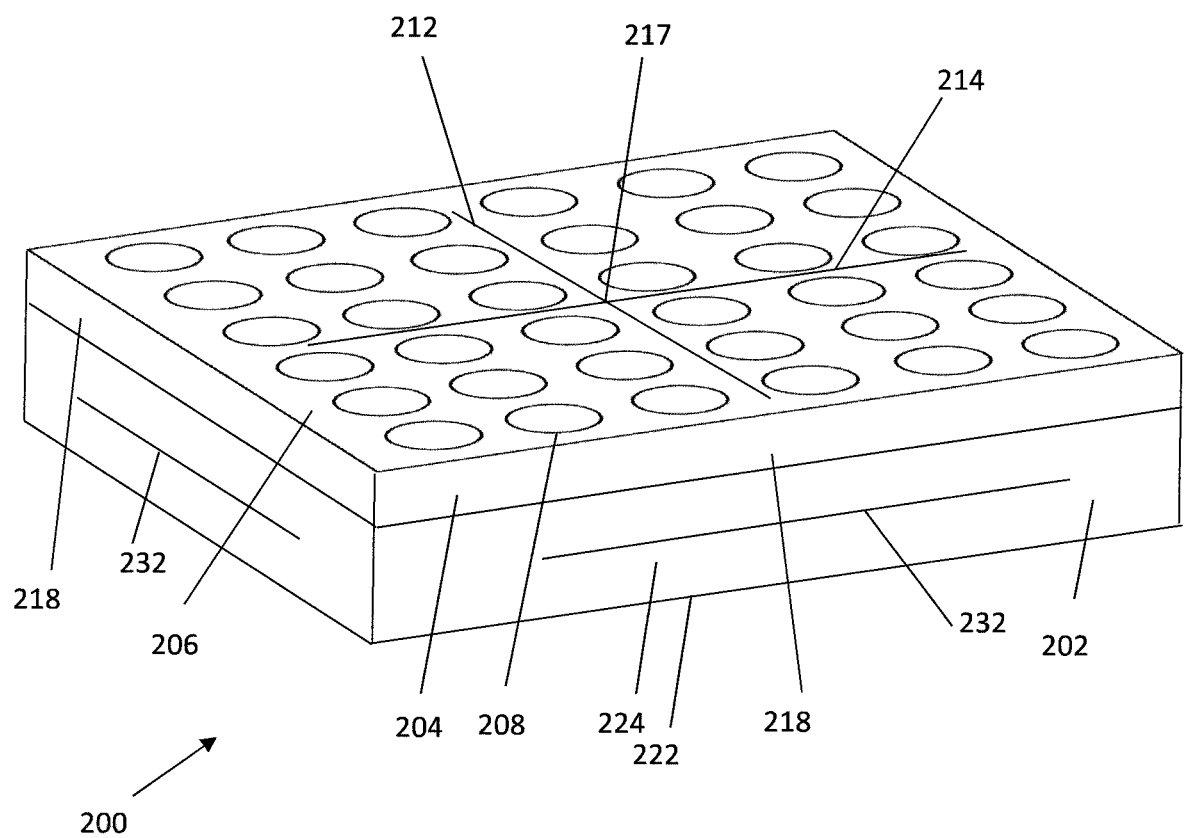
FIG. 14 is a perspective view of an assembled alternative calibration object.
Figure 15:
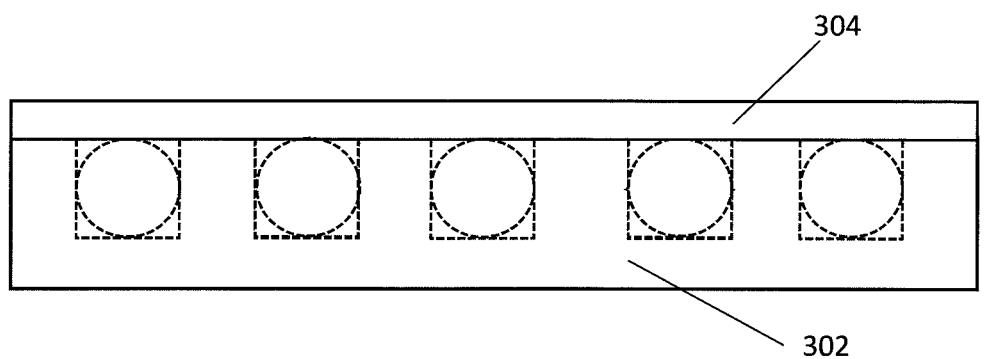
FIG. 15 is a side view of a transparent inner portion of an alternative calibration object.
Figure 16:
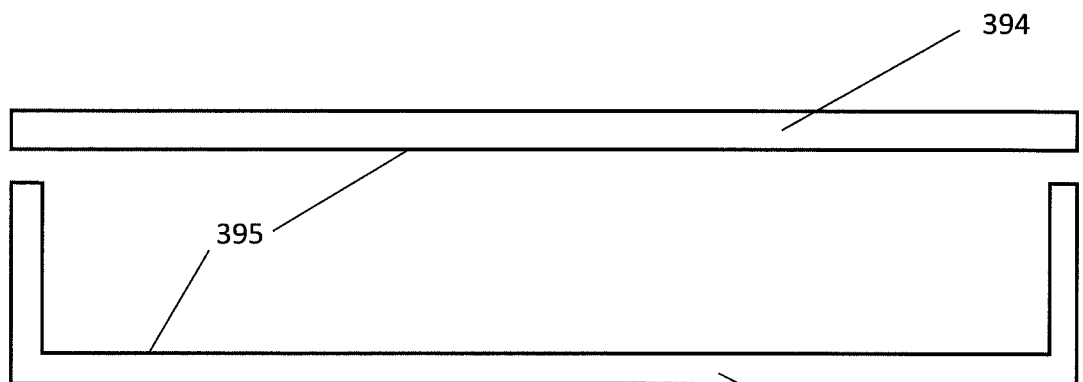
FIG. 16 is a side view of an outer portion of the alternative calibration object of FIG. 15 prior to assembly.
Figure 17:
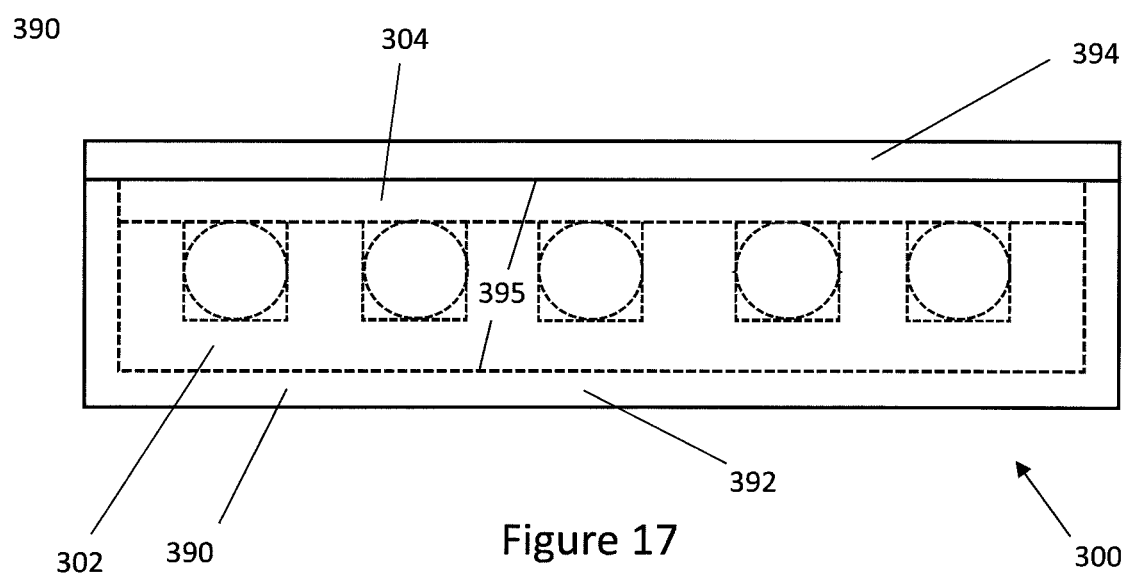
FIG. 17 is a side view of the assembled alternative calibration object of FIGS. 15 and 16.

By way of example, FIG. 14 shows an alternative calibration object 200 which is identical to calibration object 100 except that only horizontal slots 232 are provided in sides 224. It will be understood that by only providing horizontal slots, only vertical alignment of the calibration object can be achieved, i.e. confirmation that the object is flat and at the correct height. It will be understood that horizontal or vertical slots, or a combination of both horizontal and vertical slots can be incorporated onto different or the same sides to enable positioning of the calibration object.

In the calibration objects 100,200 described above, the calibration markings in the form of recesses 108,208 and slots 112,114,212,214 are provided on the upper surface 106,206. In alternative embodiments, the recesses and slots can additionally or alternatively be provided on other surfaces of the calibration object, for example, on the bottom face 122,222. Providing the recesses and slots on the bottom face is particularly advantageous when the calibration object is used in conjunction with a mechanical couch having an aperture designed to accommodate patients undergoing radiotherapy treatment for breast cancer, where images are obtained and radiation is applied from underneath the couch.

Referring to FIGS. 15 to 18, an alternative calibration object 300 will now be described.

The calibration object 300 comprises a transparent inner portion comprising a lid 304 and a base 302 section which are identically configured and assembled in the same way as the base section 102 and lid section 104 of the calibration object 100 of the first embodiment.

The assembled transparent inner portion 302,304 is then inserted into an aluminum box 390 having a base section 392 and a lid section 394 (FIG. 16, which shows the lid section 394 positioned above the base section 392) which is sized to create a tightly tolerance fit with the assembled lid 304 and base 302 sections.

Prior to the insertion of the assembled transparent inner portion 302,304 white or light colored paint is applied to an internal surface 395 of the aluminum box 390. The lid section 394 of the aluminum box 390 is positioned on and secured to the base section 392 (see FIG. 17) using a suitable fixing means such as an adhesive (not shown in FIG. 17).

Figure 18:
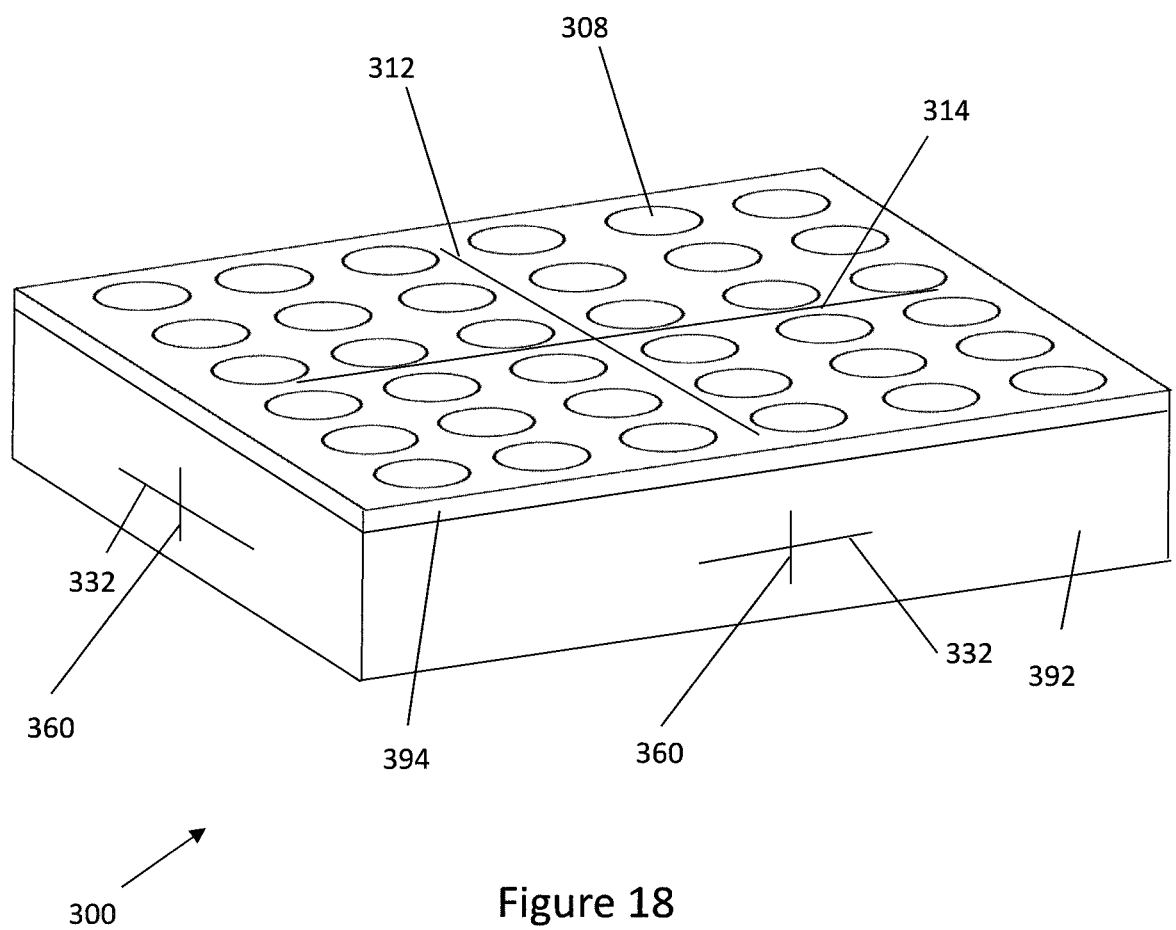
FIG. 18 is a perspective view of the assembled alternative calibration object of FIG. 17.

The calibration markings in the form of recesses 308, and positioning markings in the form of horizontal 332 and vertical 360 slots are created by precision machining the aluminum box 390 through its entire thickness, including the white coating on its internal surface 395, to reveal the transparent material. The same machining process is then used to reveal etched slots 312,314 from the lid section 394. (FIG. 18).

It will be understood that providing the aluminum box and removing the aluminum material to create the calibration and positioning markings is an alternative method to that described in relation to calibration object 100 in FIGS. 4 to 10 where the paint is removed by etching. It will also be understood the it is the aluminium material of the calibration object 300 remaining after being machined to reveal the recesses that is an opaque portion, (whereas in the calibration object 100 of FIGS. 4 to 10 it is the remaining paint after the recesses have been etched away which is an opaque portion). Either method results in highly accurate and uniform markings on the calibration object being created due to the precision machining process used to remove the opaque paint or solid aluminium material, and the high contrast between the transparent material and the remaining paint or aluminium material, which is further enhanced when the calibration object is back-illuminated as described above, and the contrast between the transparent material the remaining paint or aluminium material increases.

It will also be understood that by applying the white coating to the internal surface 395 of the aluminium box, any light from an external or internal light source will be reflected from the internal surface and back-illuminate the recesses 308.

In an alternative embodiment, the aluminum box need not be painted white, instead, the reflective nature of the aluminum material will reflect any incident light to back illuminate the calibration markings to a certain extent.

In some embodiments that rather than back-illuminating the transparent calibration markings using the laser lighting system, an alternative light source such as a LED source could be provided located inside the object. Such a light source can be turned on in a number of different ways, for example, by transmission of a signal from the camera system once it is activated, a manual switch positioned on the calibration object 100 or on the treatment apparatus, or a pressure or proximity sensor which turns on the light when the calibration object 100 is placed on the couch ready for imaging.

In the above embodiments, a calibration object 100 including radio-opaque targets or spheres has been described. It will be appreciated that including such targets enables the location of a treatment room iso-center to be identified with very high accuracy.

A calibration object 100 which did not include such radio-opaque targets or spheres could still perform a useful function. More specifically, a calibration object 100 which did not include such radio-opaque targets or spheres could be utilized to determine internal characteristics (e.g. lens distortions) of cameras of a monitoring system with the described calibration object 100 providing a high contrast high accuracy pattern which facilitated determining such internal characteristics. It will also be appreciated that such a calibration object 100 could be utilized to perform a quality control check on the accuracy of a laser lighting system by comparing the positioning of the object 100 which maximized the laser light incident on the object with the position and orientation of the object as modelled by the monitoring system. It will, however, be appreciated that such an embodiment would not enable the accuracy of the laser lighting system to be monitored to the same degree of accuracy as would be possible if radio-opaque targets or spheres are included in the calibration object 100.

Providing a calibration object of a known size and shape containing radio-opaque targets, facilitates identification of the treatment room iso-center either by irradiating the opaque targets as described in Vision RT's US Patent Application US 2016/129283, or alternatively by using the monitoring system alone to determine the location of the calibration object 100 and adjusting the position of the object either manually or using the adjustable couch 18 to position the calibration object 100 centered on the treatment room iso-center. With the calibration object 100 in place, the accuracy with which the laser lighting system highlights the treatment room iso-center could be determined. It would, however, be appreciated that if a calibration object were to be positioned solely utilizing the monitoring system without irradiating the radio-opaque markers such approach would be reliant upon the accuracy of the monitoring system. The advantage of being able to identify the iso-center without relying on irradiating the radio-opaque targets is that repeated irradiation over time degrades the radio-opaque targets to the extent they cannot be relied on for accurate imaging, and therefore by combining both radio-opaque targets and the calibration markings on the same calibration object, either method can be used, and the life of the radio-opaque targets prolonged.

It will also be appreciated that rather than positioning a calibration object 100 on the basis of feedback from the monitoring system or processing images from the irradiation of the calibration object 100, a calibration object 100 could be positioned by aligning the calibration object 100 using the laser lighting system and then the accuracy of the laser lighting system could be verified by imaging or irradiating the calibration object 100 to determine the relative positioning of the calibration object 100 and the treatment room iso-center.

In an even further embodiment, the multi-purpose object can also be used in a method of determining the accuracy of the laser lighting system operable to highlight a radiotherapy treatment apparatus iso-center. Such method comprises the steps of initially positioning the object substantially at an iso-center of the treatment apparatus; selectively allowing light from one of the plurality of laser light sources to be received by the calibration object; and adjusting the position of the light from one of the plurality of laser light sources until the quantity of light received by the calibration object corresponds to a quantity of light associated with the calibration object being positioned at the iso-center of the treatment apparatus.

Further, such accuracy measure method includes the steps of measuring a quantity of light received by the calibration object from one of the plurality of laser light sources, and comparing the measured quantity of light received with a reference quantity of light corresponding to a quantity of light received when the calibration object is positioned at the iso-center to determine when the quantity of light received by the calibration object corresponds to a quantity of light associated with the calibration object being positioned at the iso-center of the treatment apparatus.

Another method for determining the accuracy of a laser lighting system operable to highlight a radiotherapy treatment apparatus iso-center includes the steps of: positioning the calibration object centered on the position of an assumed iso-center, selectively allowing light from one of the plurality of laser light sources to be received by the calibration object, measuring a quantity of light received by the calibration object from one of the plurality of laser light sources, adjusting the position of the calibration object until the measured quantity of light is maximized, determining the position of the calibration object relative to the iso-center at the maximized light position, and comparing the position of the calibration object at the maximized light position to the iso-center position.

The calibration object may contain one or more radio-opaque targets and in which determining the position of the calibration object relative to the iso-center comprises the steps of irradiating the at least one radio-opaque target, obtaining images of the irradiated target, and analyzing the obtained images.

Furthermore, the determining of the position of the calibration object relative to the iso-center may comprise the steps of providing a patient monitoring system, imaging the calibration object using images detectors from the patient monitoring system, and generating a model of the calibration object using the obtained images.

In addition, the step of selectively allowing light from one of the plurality of laser light sources to be received by the calibration object may comprise activating only one of the plurality of laser light sources.

Alternatively, the step of selectively allowing light from one of the plurality of laser light sources to be received by the calibration object may comprise selectively preventing all but one of the plurality of laser light sources from being received by the calibration object.

To ensure that light from the laser lighting system only enters the calibration object through one of the positioning markings to ensure consistency in the comparison with the reference light value, a cover is provided which cove is positioned on the calibration object, in which the cover is configured to selectively prevent all but one of the plurality of laser light sources from being received by the calibration object.

The cover may include at least one selectively closable aperture.

The positioning of the cover on the calibration object may be done such that the at least one selectively closable aperture is adjacent the transparent portion of the positioning markings and opening the closable aperture such that light from the laser lighting system is transmitted via the aperture into the internal space of the calibration object.

The invention claimed is:

1. A multi-purpose object for a patient treatment system, said object comprising:
   a first section; and
   a second section, wherein
   said first section has an upper surface configured with a plurality of transparent markings and a lower surface configured to be arranged on a top face of said second section,
   an arrangement of first recesses is formed above said first section so as to expose said plurality of transparent markings,
   said second section comprises one or more second recess(es) configured with a depth and a width to contain a radio-opaque target object,
   said first and second sections are made from a transparent material, and
   at least one or more of a surface of an outer portion of said multi-purpose object is configured with a first light-reflective coating at areas different from positions of said transparent markings and is configured to reflect light incident on an internal space of said multi-purpose object.

2. Multi-purpose object according to claim 1, wherein the first section comprises a coating configured as a light-opaque coating, wherein said light-opaque coating is covering one or more surfaces of the first section in areas different from positions of said transparent markings.

3. Multi-purpose object according to claim 1, wherein each of said target objects is positioned in the same horizontal plane within said second recess(es).

4. Multi-purpose object according to claim 1, further comprising a light meter housed within said first and/or second section.

5. Multi-purpose object according to claim 1, further comprising an internal light source positioned within or adjacent to the first and/or second section, said light source being operable to illuminate internal parts of said first and/or second section, when said object is imaged by a camera system of said patient tracking system.

6. Multi-purpose object according to claim 5, further comprising a receiver, which is configured to automatically activate said light source upon receiving a signal from said camera system.

7. Multi-purpose object according to claim 6, wherein said multi-purpose object comprises a sensor, which sensor is configured to automatically activate said internal light source, upon sensing a positioning of said object onto a mechanical couch of said patient tracking system.

8. Multi-purpose object according to claim 5, wherein said internal light source is positioned within said first and/or second section so as to illuminate said transparent markings, when said multi-purpose object is imaged by a camera system of said patient tracking system.

9. Method of calibrating and/or monitoring a patient treatment system comprising one or more image detectors, said method including the steps of:
- providing a multi-purpose object according to claim 1;
- positioning said multi-purpose object in a patient treatment system;
- illuminating said multi-purpose object when said multi-purpose object is positioned in said patient treatment system, wherein said transparent markings are lit up by said illumination;
- imaging said multi-purpose object to obtain pattern image created via said illuminated transparent markings on said multi-purpose object.

10. Method according to claim 9, wherein in a further step said multi-purpose object is further configured to be positioned substantially at an iso-center of said patient treatment system; wherein further steps include:
- subsequently irradiating said multi-purpose object;
- obtaining irradiated images of said multi-purpose object;
- determining the relative location of said targets within the multi-purpose object by analysing said irradiated images of said multi-purpose object.

11. Method according to claim 9, wherein said multi-purpose object is positioned substantially at the iso-center of said patient treatment system, wherein further said illumination is configured as laser light, wherein when illuminated by said laser light, said multi-purpose object is configured to allow said laser light to be reflected inside said multi-purpose object, wherein said reflected light lit up the pattern created via said transparent markings.

12. Method according to claim 9, wherein further
- said irradiated images and said pattern images are utilized as input to a model generator, wherein said model generator is configured to
- utilise said pattern images to determine a positioning of a set of image detectors and a set of intrinsic parameters of said camera system and to
- utilise said irradiated images to process said irradiated images to determine the location of a treatment room iso-center.

13. A multi-purpose object for a patient treatment system, said multi-purpose object comprising:
- a first section;
- a second section; and
- a light meter housed within said first and/or second section, wherein
- said first section comprises a surface configured with a plurality of transparent markings,
- said second section has one or more recess(es) configured with a depth and a width to contain a target object, and
- said first section is configured to be arranged on top of said second section.

14. Multi-purpose object according to claim 13, wherein an internal light source is positioned within said first and/or second section so as to illuminate said transparent markings, when said multi-purpose object is imaged by a camera system of said patient tracking system.

15. A multi-purpose object for a patient treatment system, said multi-purpose object comprising:
- a first section;
- a second section; and
- an internal light source positioned within or adjacent to said first section and/or said second section, wherein
- said first section comprises a surface configured with a plurality of transparent markings,
- said second section has one or more recess(es) configured with a depth and a width to contain a target object, and
- said light source is operable to illuminate internal parts of said first and/or second section, when said multi-purpose object is imaged by a camera system of said patient tracking system.

16. Multi-purpose object according to claim 15, wherein said multi-purpose object furthermore comprises a receiver, which is configured to automatically activate said light source upon receiving a signal from said camera system.

17. Multi-purpose object according to claim 15, wherein said multi-purpose object comprises a sensor, which sensor is configured to automatically activate said internal light source, upon sensing a positioning of said object onto a mechanical couch of said patient tracking system.

* * * * *